United States Patent

Oberdorf et al.

[11] Patent Number: 6,153,560
[45] Date of Patent: Nov. 28, 2000

[54] PYRIMIDYL PHENYL AND BENZYL ETHERS, PROCESS AND INTERMEDIATE PRODUCTS FOR THEIR PRODUCTION AND THEIR USE AS HERBICIDE

[75] Inventors: Klaus Oberdorf, Heidelberg; Wassilios Grammenos, Ludwigshafen; Hubert Sauter, Mannheim; Thomas Grote, Schifferstadt; Bernd Müller, Frankenthal; Reinhard Kirstgen, Neustadt; Herbert Bayer, Mannheim; Arne Ptock, Ludwigshafen; Michael Rack, Heidelberg; Albrecht Harreus, Ludwigshafen; Franz Röhl, Schifferstadt; Eberhard Ammermann, Heppenheim; Volker Harries, Frankenthal; Gisela Lorenz, Hambach; Siegfried Strathmann, Limburgerhof, all of Germany

[73] Assignee: BASF Aktiengesellschaft, Ludwigshafen, Germany

[21] Appl. No.: 09/142,687

[22] PCT Filed: Mar. 6, 1997

[86] PCT No.: PCT/EP97/01123

§ 371 Date: Sep. 9, 1998

§ 102(e) Date: Sep. 9, 1998

[87] PCT Pub. No.: WO97/33874

PCT Pub. Date: Sep. 18, 1997

[30] Foreign Application Priority Data

Mar. 12, 1996 [DE] Germany .......................... 196 09 618

[51] Int. Cl.⁷ .......................... A01N 43/54; C07D 239/02
[52] U.S. Cl. .......................... 504/240; 504/242; 544/298; 544/299
[58] Field of Search ..................... 544/299, 298; 504/240, 242

[56] References Cited

U.S. PATENT DOCUMENTS 5,438,059  8/1995  Clough et al. .......................... 514/256

*Primary Examiner*—Mukund J. Shah
*Assistant Examiner*—Sudhaker B. Patel
*Attorney, Agent, or Firm*—Keil & Weinkauf

[57] ABSTRACT

Pyrimidyl phenyl and pyrimidyl benzyl ethers of the general formula I

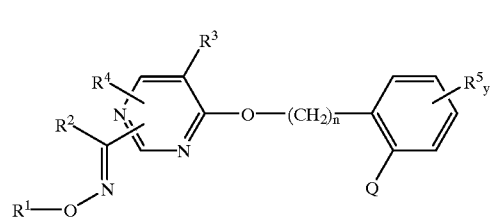

and their salts and N-oxides, where the substituents and indices have the following meanings:

Q is $(CO_2CH_3)$=$CHCH_3$, $C(CO_2CH_3)$=$CHOCH_3$, $C(CONHCH_3)$=$CHOCH_3$, $C(CONH_2)$=$NOCH_3$, $C(CONHCH_3)$=$NOCH_3$ or $N(OCH_3)$—$CO_2CH_3$;

n is 0 or 1;

$R^1$ is hydrogen or an organic radical bonded via a carbon atom;

$R^2$ is hydrogen, cyano, halogen or an organic radical bonded via a carbon, oxygen, sulfur or nitrogen atom;

$R^3$ is hydrogen, halogen, $C_1$–$C_4$-alkyl or $C_1$–$C_2$-haloalkyl;

$R^4$ is hydrogen, cyano, nitro, halogen or an organic radical bonded via a carbon, oxygen, sulfur or nitrogen atom;

y is 0, 1, 2 or 3, it being possible for the radicals $R^5$ to be different if y is 2 or 3;

$R^5$ is cyano, halogen, $C_1$–$C_4$-alkyl, $C_1$–$C_4$-haloalkyl or $C_1$–$C_4$-alkoxy, processes and intermediates for their preparation, and their use.

7 Claims, No Drawings

PYRIMIDYL PHENYL AND BENZYL ETHERS, PROCESS AND INTERMEDIATE PRODUCTS FOR THEIR PRODUCTION AND THEIR USE AS HERBICIDE

DESCRIPTION

The present invention relates to pyrimidyl phenyl and pyrimidyl benzyl ethers of the general formula I

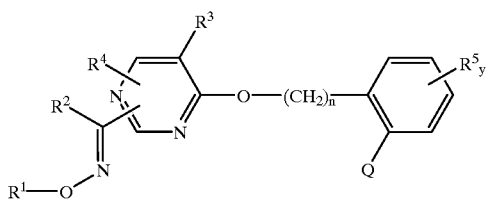

and to their salts and N-oxides where the substituents and indices have the following meanings:

Q is $C(CO_2CH_3)$=$CHCH_3$, $C(CO_2CH_3)$=$CHOCH_3$, $C(CONHCH_3)$=$CHOCH_3$, $C(CONH_2)$=$NOCH_3$, $C(CONHCH_3)$=$NOCH_3$ or $N(OCH_3)$—$CO_2CH_3$;

n is 0 or 1;

$R^1$ is hydrogen or an organic radical bonded via a carbon atom;

$R^2$ is hydrogen, cyano, halogen or an organic radical bonded via a carbon, oxygen, sulfur or nitrogen atom;

$R^3$ is hydrogen, halogen, $C_1$–$C_4$-alkyl or $C_1$–$C_2$-haloalkyl;

$R^4$ is hydrogen, cyano, nitro, halogen or an organic radical bonded via a carbon, oxygen, sulfur or nitrogen atom;

y is 0, 1, 2 or 3, it being possible for the radicals $R^5$ to be different if y is 2 or 3;

$R^5$ is cyano, halogen, $C_1$–$C_4$-alkyl, $C_1$–$C_4$-haloalkyl or $C_1$–$C_4$-alkoxy.

The invention furthermore relates to processes and intermediates for the preparation of these compounds and to their use for controlling animal pests and harmful fungi.

Pyrimidylphenyl and -benzyl ethers having fungicidal, or fungicidal and insecticidal, properties have been disclosed in the literature (EP-A 254 426; EP-A 278 595; EP-A 299 694; EP-A 363 818; EP-A 350 691; EP-A 398 692; EP-A 407 873; EP-A 477 631; EP-A 513 580; JP-A 04/182,461; WO-A 93/15,046), which differ from the compounds according to the invention by the substituents in the pyrimidyl moiety.

It was an object of the present invention to provide compounds with an improved activity and a widened spectrum of action.

We have found that this object is achieved by the compounds I defined at the outset. We have furthermore found processes and intermediates for the preparation of these compounds and their use for controlling animal pests and harmful fungi.

The compounds I are accessible via various routes by processes described per se in the literature.

The construction of the group Q is disclosed, for example, in the literature cited at the outset and is carried out in general and in particular by the processes described therein.

Usually, a procedure is followed for the synthesis of the compounds I in which a pyrimidine derivative of the formula IIa is converted with a phenol or a benzyl alcohol of the formula IIIa in an inert solvent to give the corresponding ether of the formula IVa, and IVa is subsequently reacted with an O-substituted hydroxylamine ($R^1$—O—$NH_2$) or a salt thereof to give I.

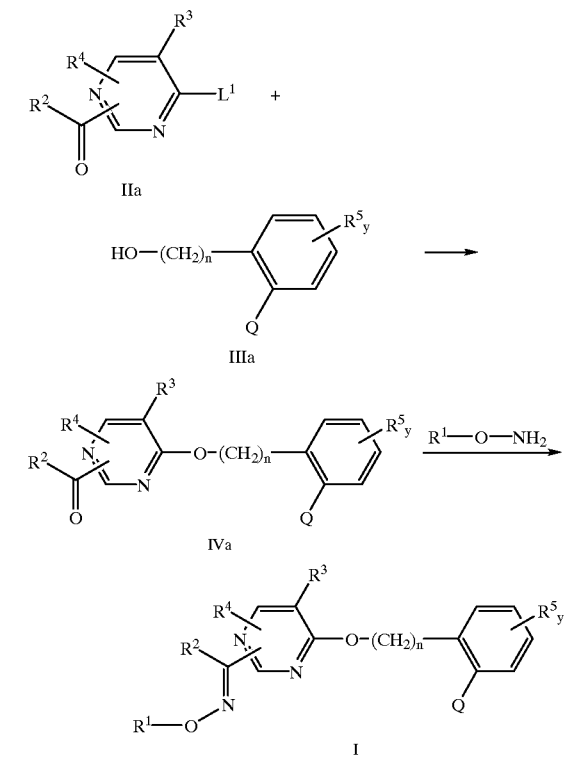

$L^1$ in formula IIa is a nucleophilically exchangeable leaving group, such as halogen (eg. fluorine, chlorine, bromine or iodine) or alkyl- or arylsulfonate (eg. methylsulfonate, trifluoromethylsulfonate, phenylsulfonate or methylphenylsulfonate).

1a) The reaction of IIa with IIIa is normally carried out in an inert solvent at from 0° C. to 130° C., preferably 20° C. to 80° C. in the presence of a base.

Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, especially preferably tetrahydrofuran, acetonitrile, dimethyl sulfoxide and acetone. Mixtures of these can also be used.

Bases which are suitable are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and alkali metal hydrogen carbonates such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alkoxides, such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyrimidines, such as collidine, lutidine and 4-dimethylaminopyridine, and bicyclic amines. Substances which are especially preferred are potassium carbonate, sodium hydride and potassium tert-butylate. In general, the bases are employed in catalytic amounts, but they can also be used in equimolar amounts, in an excess or, if desired, as the solvent.

In general, the starting materials are reacted with each other in eguimolar amounts. It may be advantageous for the yield to employ an excess of IIa based on IIIa.

1b) The reaction of IVa with the O-substituted hydroxylamine or the salt thereof is normally carried out in an inert solvent at from 0° C. to 80° C., preferably 20° C. to 60° C., in the presence or absence of an acid or in the presence or absence of a base if the O-substituted hydroxylamine is liberated from its salt.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and also dimethyl sulfoxide, dimethylformamide and pyridine, especially preferably methanol and pyridine. Mixtures of these can also be used.

Bases which are suitable are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and alkali metal hydrogen carbonates such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alkoxides, such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines, such as collidine, lutidine and 4-dimethylaminopyridine, and bicyclic amines. Substances which are especially preferred are pyridine and sodium hydroxide. The bases are generally employed in catalytic amounts, but they can also be used in equimolar amounts, in an excess or, if desired, as the solvent.

Acids and acidic catalysts which are used are inorganic acids such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium (IV) chloride and zinc(II) chloride, and organic acids such as formic acid, acetic acid, propionic acid, oxalic acid, citric acid and trifluoroacetic acid. In general, the acids are employed in catalytic amounts.

In general, the starting materials are reacted with each other in equimolar amounts. It may be advantageous for the yield to employ hydroxylamine or a salt thereof in an excess, based on IVa.

In a similar manner, the compounds I are obtained by first converting a pyrimidine derivative of the formula IIa with an O-substituted hydroxylamine ($R^1$—O—$NH_2$) or a salt thereof to give the corresponding compound of the formula Va, and subsequently reacting Va with a phenol or a benzyl alcohol of the formula IIIa in an inert solvent to give I.

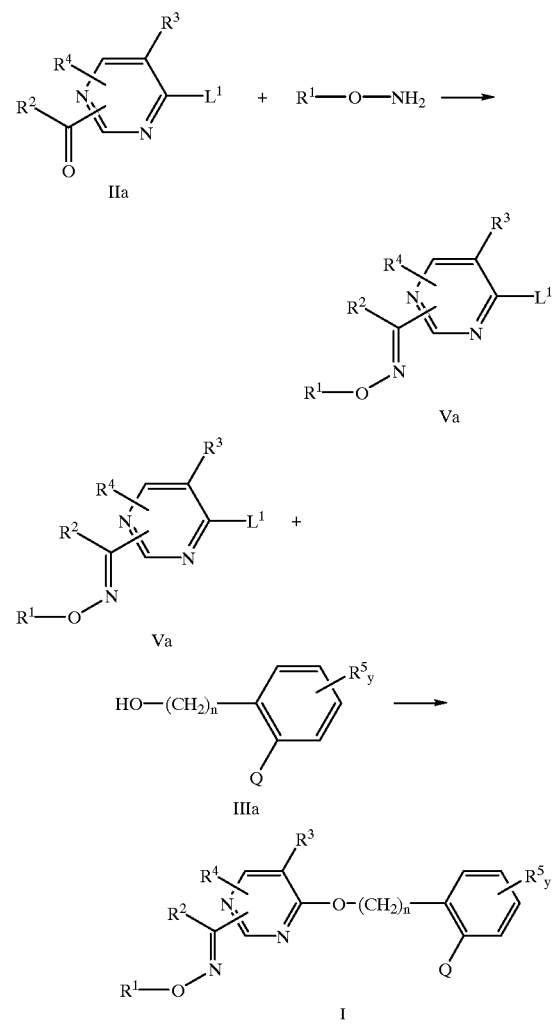

The reactions proceed in general and in particular by the methods described hereinabove.

Compounds I where n is 1 are preferably obtained by converting a pyrimidine alcohol of the formula IIb with a benzyl compound of the formula IIIb in an inert solvent to give the corresponding benzyl ether of the formula IVb, and subsequently reacting IVb with an O-substituted hydroxylamine ($R^1$—O—$NH_2$) or a salt thereof to give I.

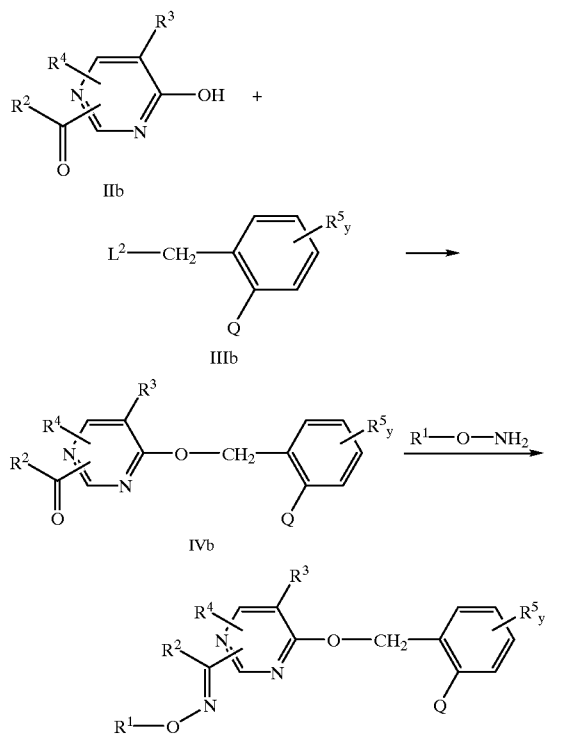

$L^2$ in formula IIIb is a nucleophilically exchangeable leaving group such as halogen (eg. chlorine, bromine or iodine) or alkyl sulfonate or aryl sulfonate (eg. methylsulfonate, trifluoromethylsulfonate, phenylsulfonate or methylphenylsulfonate).

2a) The reaction of IIb with IIIb is normally carried out in an inert solvent at from 0° C. to 130° C., preferably 20° C. to 60° C., in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, especially preferably tetrahydrofuran, acetonitrile, dimethyl sulfoxide and acetone. Mixtures of these can also be used.

Bases which are suitable are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and alkali metal hydrogen carbonates such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alkoxides, such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines, such as collidine, lutidine and 4-dimethylaminopyridine, and bicyclic amines. Substances which are especially preferred are potassium carbonate, sodium hydride and potassium tert-butylate. In general, the bases are employed in catalytic amounts, but they can also be used in equimolar amounts, in an excess or, if desired, as the solvent.

In general, the starting materials are reacted with each other in equimolar amounts. It may be advantageous for the yield to employ IIb in an excess, based on IIIb.

2b) The reaction of IVb with the O-substituted hydroxylamine or a salt thereof is carried out in general and in particular under the conditions described above under item 1b.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, alcohols such as methanol, ethanol, n-propanol, isopropanol, n-butanol and tert-butanol, and also dimethyl sulfoxide, dimethylformamide and pyridine, especially preferably methanol and pyridine. Mixtures of these can also be used.

Bases which are suitable are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and alkali metal hydrogen carbonates such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alkoxides, such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines, such as collidine, lutidine and 4-dimethylaminopyridine, and bicyclic amines. Substances which are especially preferred are pyridine and sodium hydroxide. Bases are generally employed in catalytic amounts, but they can also be used in equimolar amounts, in an excess or, if desired, as the solvent.

Acids and acidic catalysts which are used are inorganic acids such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium (IV) chloride and zinc(II) chloride, and organic acids such as formic acid, acetic acid, propionic acid, oxalic acid, citric acid and trifluoroacetic acid. In general, the acids are employed in catalytic amounts.

In general, the starting materials are reacted with each other in equimolar amounts. It may be advantageous for the yield to employ IIb in an excess, based on IIIb.

In a similar manner, the compounds I where n is 1 are obtained by first converting a pyrimidine alcohol of the formula IIb with an O-substituted hydroxylamine ($R^1$—O—$NH_2$) or a salt thereof to give the corresponding compound of the formula Vb, and subsequently reacting Vb with a benzyl compound of the formula IIIb in an inert solvent to give I.

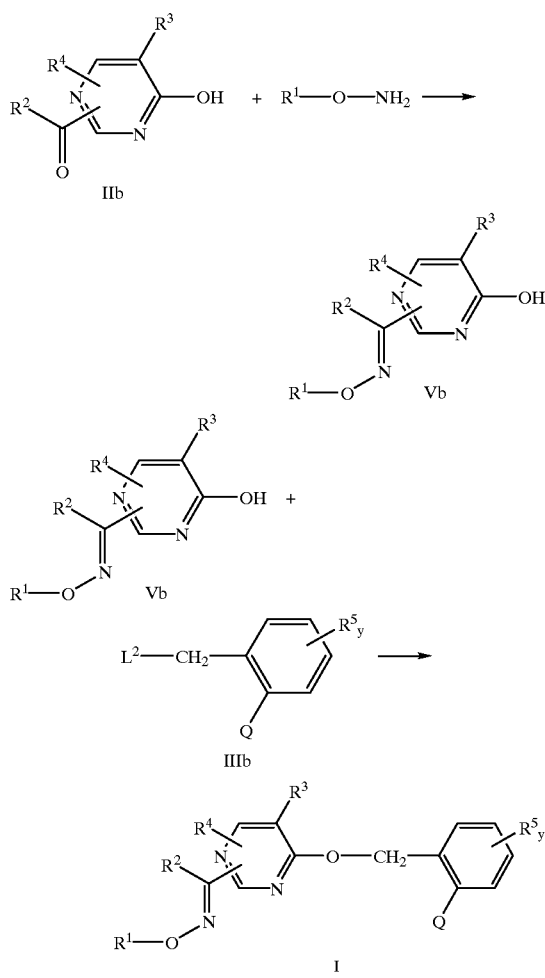

The reactions are carried out in general and in particular by the methods described above.

Those starting materials of the formulae IIIa and IIIb which are required for the preparation of the compounds I by the above-described process and which have not already been disclosed in the literature cited at the outset can be prepared in a similar manner by the processes described therein.

The starting materials of the formula IIa can be obtained by reacting a suitably substituted pyrimidine of the formula VIa with an activated carboxylic acid of the formula VIIa in an inert solvent in the presence of an organometallic base [cf. J. Organomet. Chem. 56, (1973) 53–66; Chem. Ber. 125, (1992) 1169–1190].

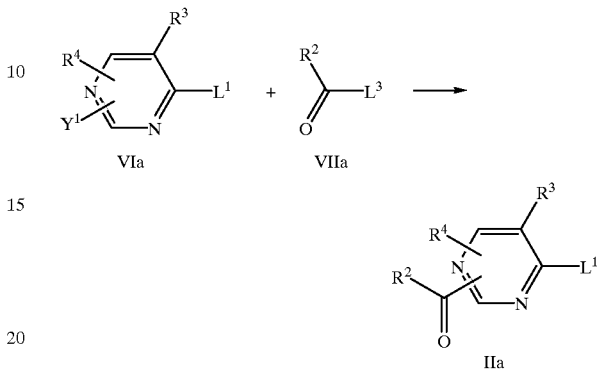

$Y^1$ in formula VIa is a halogen atom, eg. fluorine, chlorine, bromine and iodine, especially bromine and iodine.

$L^3$ in formula VII is a halogen atom, eg. fluorine, chlorine, bromine and iodine, especially chlorine, or an amide radical or an ester radical. A corresponding cyanide $R^2$—C≡N may also be employed in place of the compound VIIa.

This reaction is normally carried out in an inert solvent in the presence of an organometallic base at from −75° C. to 40° C., preferably −75° C. to 0° C.

Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, and also dimethyl sulfoxide and dimethylformamide, especially preferably diethyl ether and tetrahydrofuran. Mixtures of the abovementioned solvents may also be used.

Organometallic bases which are generally suitable are organometallic compounds, in particular alkali metal alkyls such as methyllithium, butyllithium and phenyllithium, alkylmagnesium halides such as methylmagnesium chloride. n-butyllithium is especially preferred. In general, the bases can be used in equimolar amounts or in an excess.

In general, the starting materials are reacted with each other in equimolar amounts. It may be advantageous for the yield to employ VIIa in an excess, based on VIa.

By a further method, the compounds IIa are also obtained by reacting a pyrimidinecarbonyl halide of the general formula VIIIa with an organometallic compound ($R^2$—M; M is the equivalent of a metal ion) in an inert solvent [cf. DE-A 38 38 243; EP-A 446 872].

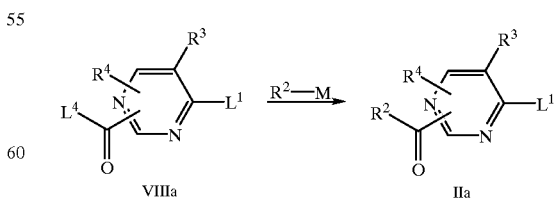

Especially suitable as metal (M) are lithium, magnesium, copper and zinc.

$L^4$ in formula VIIIa is a halogen atom, eg. fluorine, chlorine, bromine and iodine, especially chlorine.

This reaction is normally carried out in an inert solvent at from −80° C. to 20° C., preferably −75° C. to 0° C.

Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran especially preferably diethyl ether and tetrahydrofuran. Mixtures of these can also be used.

The starting materials are generally reacted with each other in equimolar amounts. It may be advantageous for the yield to employ the organometallic compound in an excess, based on VIIIa.

In a further method, the compounds IIa are also obtained by converting a pyrimidinecarbonyl halide of the general formula VIIIa with a malonic ester of the formula IX in an inert solvent to give the corresponding triketone VIIIb, and subsequently reacting VIIIb to give IIa [cf. Tetrahedron 48 (22), (1992) 9233].

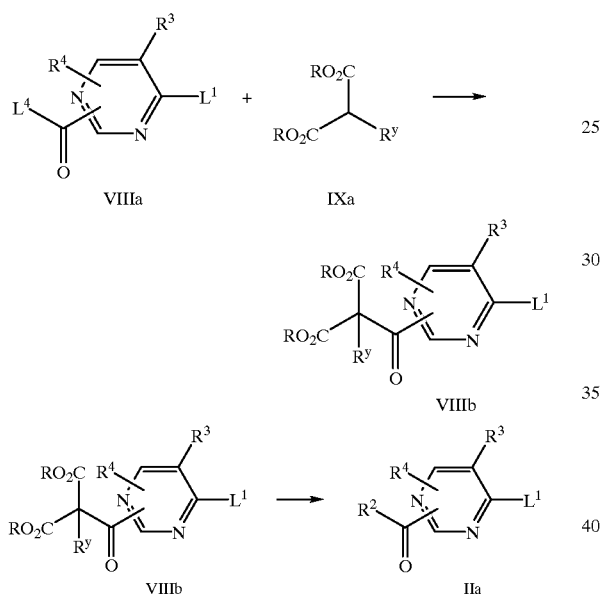

$R^y$ in formulae VIIIb and IXa is the radical of a group $R^2$.

The symbols R in formulae VIIIb and IXa are $C_1$–$C_4$-alkyl groups, which are independent of one another, in particular methyl and ethyl.

3a) The reaction of VIIIa and IXa is normally carried out in an inert solvent at from 0° C. to 120° C., preferably 20° C. to 80° C. in the presence of a base and in the presence or absence of a Lewis acid such as magnesium chloride.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide, dimethylformamide, especially preferably toluene. Mixtures of these can also be used.

Bases which are suitable are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides such as lithium amide, sodium amide and potassium amide, alkali metal carbonates and alkaline earth metal carbonates, such as lithium carbonate and calcium carbonate, and alkali metal hydrogen carbonates such as sodium hydrogen carbonate, organometallic compounds, in particular alkali metal alkyls, such as methyllithium, butyllithium and phenyllithium, alkylmagnesium halides such as methylmagnesium chloride, and alkali metal alcoholates and alkaline earth metal alkoxides, such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines, such as collidine, lutidine and 4-dimethylaminopyridine, and bicyclic amines. Especially preferred substances are sodium hydroxide and triethylamine. In general, the bases are employed in equimolar amounts, but they can also be used in an excess or, if desired, as the solvent.

In general, the starting materials are reacted with each other in equimolar amounts. It may be advantageous for the yield to employ IXa in an excess based on VIIIa.

3b) The decarboxylation of VIIIb to IIa is normally carried out in an inert solvent at from 60° C. to 200° C., preferably 100° C. to 160° C., in the presence or absence of a base.

Suitable solvents are aromatic hydrocarbons such as toluene, o-, m- and p-xylene, halogenated hydrocarbons such as chlorobenzene, nitriles such as acetonitrile and propionitrile, alcohols such as methanol, ethanol, n-propanol, isopropanol, n-butanol and tert-butanol, and also dimethyl sulfoxide and dimethylformamide, especially preferably water and dimethyl sulfoxide. Mixtures of these can also be used.

Bases which are suitable are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides such as lithium amide, sodium amide and potassium amide, alkali metal carbonates and alkaline earth metal carbonates, such as lithium carbonate and calcium carbonate, and alkali metal hydrogen carbonates such as sodium hydrogen carbonate, organometallic compounds, in particular alkali metal alkyls, such as methyllithium, butyllithium and phenyllithium, alkylmagnesium halides, such as methylmagnesium chloride, and alkali metal alcoholates and alkaline earth metal alkoxides, such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines, such as collidine, lutidine and 4-dimethylaminopyridine, and bicyclic amines. Especially preferred substances are sodium hydroxide and sodium methanolate. In general, the bases are employed in catalytic amounts, but they can also be used in equimolar amounts, in an excess or, if desired, as the solvent.

The starting materials of the formula IIb are obtained by converting a suitably substituted pyrimidine derivative of the formula VIa with an alcoholate (R'—O⁻ M⁺; R' is $C_1$-$C_4$-alkyl, M⁺ is the equivalent of an alkali metal cation or alkaline earth metal cation, in particular sodium or potassium) in the presence of a base to give the corresponding alkyl pyrimidyl ether of the formula VIb, subsequently converting VIb by a method similar to the above-described process (reaction of VIa) into the corresponding ether IIc by reaction with an activated carboxylic acid of the formula VIIa, and subsequently cleaving IIc to give IIb.

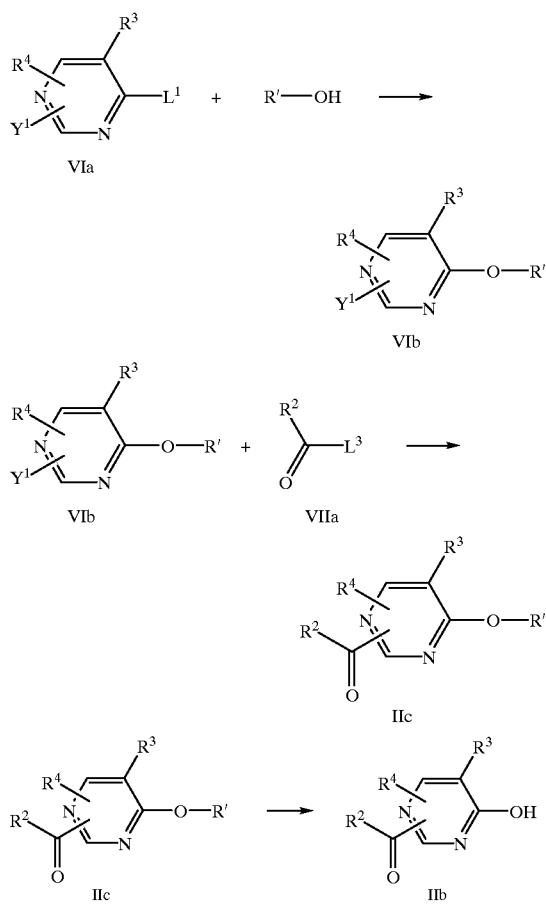

4a) The etherification of VIa to VIb is normally carried out at from 0° C. to 120° C., preferably 20° C. to 80° C., in the presence of an inert solvent.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, especially preferably dimethylformamide. Mixtures of these can also be used.

In general, the pyrimidine derivative VIa and the alcoholate are reacted with each other in equimolar amounts. It may be advantageous for the yield to employ the alcoholate in an excess, based on VIa, or as the solvent.

4b) The reaction of the ether VIb with the activated carboxylic acid VIIa is carried out in general and in particular under the conditions described for the preparation of the compounds IIa from the compounds VIa.

4c) The ether cleavage of IIc to IIb is normally carried out at from 0° C. to 130° C., preferably 60° C. to 100° C., in an inert solvent in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, nitriles such as acetonitrile and propionitrile, alcohols such as methanol, ethanol, n-propanol, isopropanol, n-butanol and tert-butanol, and also dimethyl sulfoxide and dimethylformamide, especially preferably methylene chloride. Mixtures of these can also be used.

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium (IV) chloride and zinc(II) chloride, and organic acids such as formic acid, acetic acid, propionic acid, oxalic acid, citric acid and trifluoroacetic acid. In general, the acids are employed in catalytic amounts, but they can also be used in equimolar amounts, in an excess, or, if desired, as the solvent.

Moreover, the intermediates of the formula IVa can be obtained by reacting an ether of the formula Xa either (a) with an activated carboxylic acid of the formula VIIb in an inert solvent in the presence of an organometallic base or (b) with an organotin compound of the formula XI in an inert solvent.

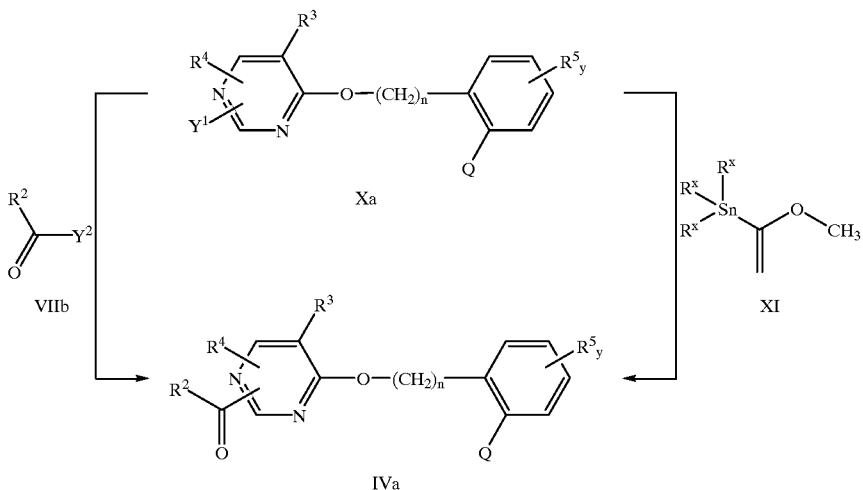

$Y^1$ in formula Xa is a halogen atom, such as fluorine, chlorine, bromine and iodine, in particular bromine and iodine.

$Y^2$ in formula VIIb is a halogen atom such as fluorine, chlorine, bromine and iodine, in particular chlorine.

The radicals $R^x$ in formula XI are independent of one another and are alkyl.

5a) The reaction of the ether Xa with the activated carboxylic acid VIIb is carried out in general and in particular under the conditions described for the preparation of the compounds IIa from the compounds VIa.

5b) The reaction of the ether Xa with the organotin compound XI is normally carried out at from −70° C. to 40° C., preferably −70° C. to 0° C. in an inert solvent in the presence of a catalyst such as $Pd[P(C_6H_5)_3]_3$ and $PdCl_2$.

Suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, nitrites such as acetonitrile and propionitrile, and also dimethyl sulfoxide and dimethylformamide, especially preferably tetrahydrofuran and diethyl ether. Mixtures of these can also be used.

In general, the starting materials are reacted with each other in equimolar amounts. It may be advantageous for the yield to employ the organotin compound XI in an excess, based on the ether Xa.

The intermediates of the formula Vc are preferably obtained by nitrozating an alkyl pyrimidyl ether VIIIe to give Vd and subsequently reacting Vd with a reagent $R^1$—$Y^5$ to give Vc.

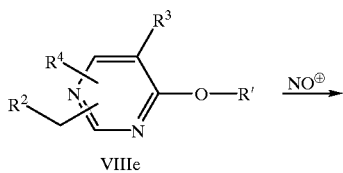

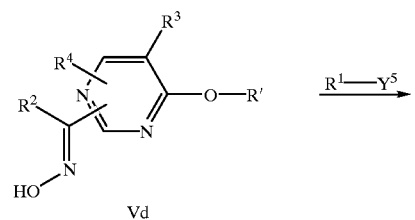

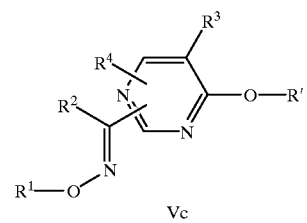

$Y^5$ is a nucleophilically exchangeable leaving group such as halogen (eg. fluorine, chlorine, bromine or iodine) or alkyl- or arylsulfonate (eg. methylsulfonate, trifluoromethylsulfonate, phenylsulfonate or methylphenylsulfonate).

6a) The nitrozation of VIIIe to Vd is normally carried out in general and in particular following the processes described in the literature [cf. Houben-Weyl, E14b, Part 1, page 287 et seq. and Liebigs Ann. Chem. 737 (1970), 39].

6b) The etherification of Vd to Vc is normally carried out in general and in particular following the processes described in the literature [cf. Houben-Weyl, E14b, Part 1, page 370 et seq.].

By a further preferred process, the compounds Vc are obtained by converting a β-dicarbonyl of the formula XII with an amidine, guanidine, urea or thiourea of the formula XIII to give the corresponding pyrimidine VIIId', hydrolyzing VIIId' to give the ketone VIIIc and subsequently reacting VIIIc with an O-substituted hydroxylamine ($R^1$—O—$NH_2$) or salt thereof to give I.

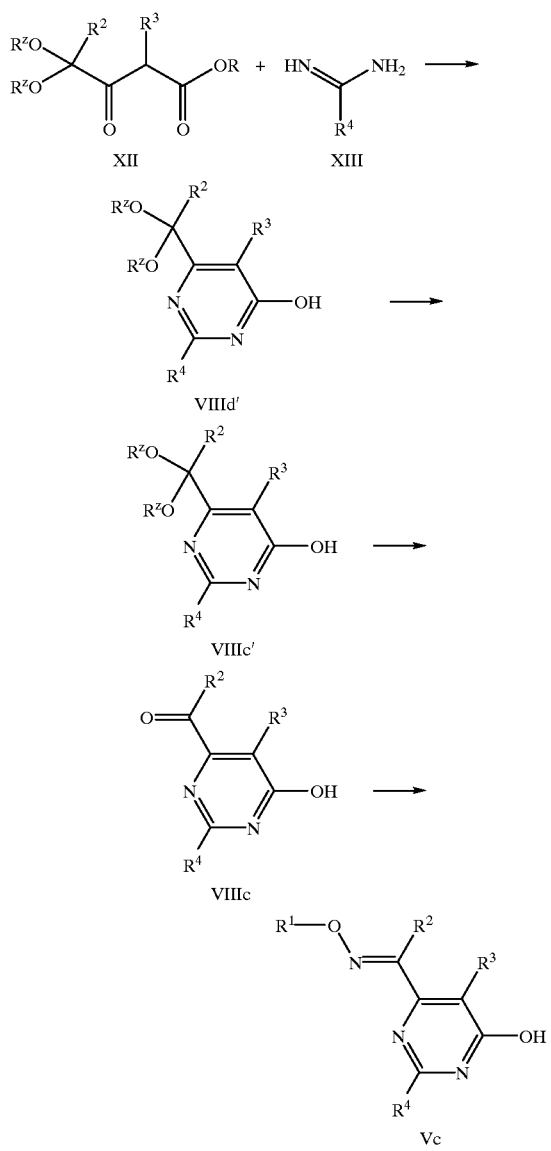

R in formula XII is an alkyl radical having 1 to 4 carbon atoms, preferably methyl or ethyl.

The symbols $R^z$ in formulae XII, VIIId' and VIIIc' are alkyl groups, preferably having 1 to 4 carbon atoms, in particular methyl and ethyl; the two groups $R^z$ can also together be an ethylene or propylene chain.

7a) The reaction of XII with XIII is normally carried out at from 0 to 120° C., preferably 20 to 80° C., in particular at the boiling point of the solvent. Solvents which are normally used are alcohols, in particular methanol or ethanol.

The compounds XIII can also be employed in the form of their salts, in particular as hydrohalides (eg. hydrochloride or hydrobromide). If salts are used, it is recommended to carry out the reaction in the presence of a base (eg. alkaline earth metal alkoxides, alkaline earth metal hydroxides, alkali metal alkoxides or alkali metal hydroxides, such as sodium methoxide, sodium ethoxide, potassium tert-butoxide, sodium hydroxide, potassium hydroxide and calcium hydroxide).

7b) The hydrolysis of VIIId to VIIIc is normally carried out from 0° C. to 130° C., preferably 20° C. to 110° C., in an inert solvent in the presence of an acid.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol and also dimethyl sulfoxide and dimethylformamide, especially preferably dioxane. Mixtures of these may also be used.

Acids and acidic catalysts which are used are inorganic acids such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium (IV) chloride and zinc(II) chloride, especially preferably hydrochloric acid, and also organic acids such as formic acid, acetic acid, propionic acid, oxalic acid, citric acid and trifluoroacetic acid. In general, the acids are employed in catalytic amounts, but they can also be used in equimolar amounts, in an excess, or, if desired, as the solvent.

7c) The oximation of VIIIc to Vc is carried out in general and in particular under the conditions described above under item 2b) for the preparation of I from IVb.

When preparing compounds I according to the invention, it is generally irrelevant whether the starting materials and intermediates containing the phenyl or the benzyl moiety (formulae III, IV and X) and the ethers of the formula I already contain the group Q or whether this position is occupied by a group which can be converted into Q by the processes described in the literature cited at the outset. In principle the group Q can be synthesized at any of the levels mentioned (formulae II, IV, X and I).

In the novel intermediates of the general formula II,

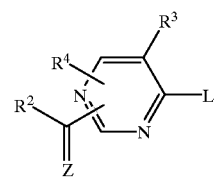

II the substituents $R^2$, $R^3$ and $R^4$ and the index x have the meaning given at the outset and L and Z are the following groups:

L is hydroxyl or a nucleophilically exchangeable leaving group;

Z is oxygen or a group $NOR^1$, $R^1$ having the meaning given at the outset.

In the novel intermediates of the general formula X

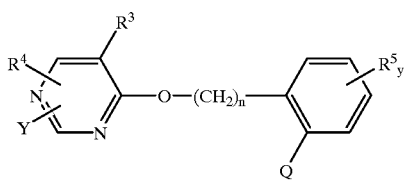

the substituents Q, $R^2$, $R^3$, $R^4$ and $R^5$ and the indices n, x and y have the meanings given at the outset and Y is one of the following groups: halogen or CO—$R^2$, $R^2$ having the meaning given at the outset.

The reaction mixtures are worked up in the customary manner, eg. by mixing with water, phase separation and, if desired chromatographic purification of the crude products. In some cases, the intermediates and end products are obtained in the form of colorless or pale brown viscous oils, which are purified or freed from volatile components under reduced pressure and moderately elevated temperatures. If the intermediates and end products obtained are solids, they may also be purified by recrystallization or digestion.

Due to their C=C— and C=N-double bonds the compounds I can be obtained from their preparation in the form of E/Z isomer mixtures, which can be separated into the individual compounds in the customary manner, eg. by crystallization or chromatography.

If isomer mixtures are obtained from the synthesis, however, a separation is generally not absolutely necessary, since in some cases individual isomers can be converted into each other during formulation for use, or upon use (eg. when exposed to light, acids or bases). Similar conversions can also take place after application, for example in the treatment of plants in the treated plant or in the harmful fungus or animal pest to be controlled.

With regard to their activity, the E isomers of the compounds I are preferred as far as the C=$NOR^1$ double bond is concerned (configuration based on the $R^2$ group relative to the $OR^1$ group).

In the definitions of the symbols mentioned in the above formulae, collective terms were used which generally represent the following substituents:

Halogen: fluorine, chlorine, bromine and iodine;

Alkyl: saturated, straight-chain or branched hydrocarbon radicals having 1 to 4, 6, 8 or 10 carbon atoms, eg. $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 10 carbon atoms (as mentioned above), it being possible for some or all of the hydrogen atoms in these groups to be replaced by halogen atoms as mentioned above, eg. $C_1$—$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 10 carbon atoms (as mentioned above) which are linked to the skeleton via an oxygen atom (—O—);

Haloalkoxy: straight-chain or branched haloalkyl groups having 1 to 10 carbon atoms (as mentioned above) which are linked to the skeleton via an oxygen atom (—O—);

Alkylthio: straight-chain or branched alkyl groups having 1 to 10 or 1 to 4 carbon atoms (as mentioned above) which are linked to the skeleton via a sulfur atom (—S—);

Alkylamino: a straight-chain or branched alkyl group having 1 to 10 carbon atoms (as mentioned above) which is linked to the skeleton via an amino group (—NH—);

Dialkylamino: two straight-chain or branched alkyl groups, independent of one another, having in each case 1 to 10 carbon atoms (as mentioned above) and being linked to the skeleton via a nitrogen atom;

Alkylcarbonyl: a straight-chain or branched alkyl group having 1 to 10 carbon atoms (as mentioned above) which is linked to the skeleton via a carbonyl group (—CO—);

Alkoxycarbonyl: an alkoxy group having 1 to 10 carbon atoms (as mentioned above) which is linked to the skeleton via a carbonyl group (—CO—);

Alkylthiocarbonyl: an alkylthio group having 1 to 10 carbon atoms (as mentioned above) which is linked to the skeleton via a carbonyl group (—CO—);

Alkylaminocarbonyl: an alkylamino group having 1 to 10 carbon atoms (as mentioned above) which is linked to the skeleton via a carbonyl group (—CO—);

Dialkylaminocarbonyl: a dialkylamino group (as mentioned above), which is linked to the skeleton via a carbonyl group (—CO—);

Alkylcarbonyloxy: a straight-chain or branched alkyl group having 1 to 10 carbon atoms (as mentioned above) which is linked to the skeleton via a carbonyloxy group (—$CO_2$—);

Alkylcarbonylthio: a straight-chain or branched alkyl group having 1 to 10 carbon atoms (as mentioned above) which is linked to the skeleton via a carbonylthio group (—COS—);

Alkylcarbonylamino: a straight-chain or branched alkyl group having 1 to 10 carbon atoms (as mentioned above) which is linked to the skeleton via a carbonylamino group (—CONH—);

Alkylsulfonyl: a straight-chain or branched alkyl group having 1 to 10 carbon atoms (as mentioned above) which is linked to the skeleton via a sulfonyl group (—$SO_2$—);

Alkoxysulfonyl: an alkoxy group having 1 to 10 carbon atoms (as mentioned above) which is linked to the skeleton via a sulfonyl group (—$SO_2$—);

Alkylthiosulfonyl: an alkylthio group having 1 to 10 carbon atoms (as mentioned above) which is linked to the skeleton via a sulfonyl group (—$SO_2$—);

Alkylaminosulfonyl: an alkylamino group having 1 to 10 carbon atoms (as mentioned above) which is linked to the skeleton via a sulfonyl group (—$SO_2$—);

Dialkylaminosulfonyl: a dialkylamino group (as mentioned above) which is linked to the skeleton via a sulfonyl group (—$SO_2$—);

Alkenyl: unsaturated, straight-chain or branched hydrocarbon radicals having 2 to 4, 6, 8 or 10 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated, straight-chain or branched hydrocarbon radicals having 2 to 10 carbon atoms and a double bond in any position (as mentioned above), it being possible for some or all of the hydrogen atoms in these groups to be replaced by halogen atoms as mentioned above, in particular fluorine, chlorine and bromine;

Alkenyloxy: unsaturated, straight-chain or branched hydrocarbon radicals having 3 to 10 carbon atoms and a double bond in any position which is not adjacent to the hetero atom (as mentioned above) which are linked to the skeleton via an oxygen atom (—O—);

Haloalkenyloxy: unsaturated, straight-chain or branched alkenyloxy groups having 3 to 10 carbon atoms (as mentioned above), it being possible for some or all of the hydrogen atoms in these groups to be replaced by halogen atoms as mentioned above, in particular fluorine, chlorine and bromine;

Alkenylthio: unsaturated, straight-chain or branched hydrocarbon radicals having 3 to 10 carbon atoms and a double bond in any position which is not adjacent to the hetero atom (as mentioned above) which are linked to the skeleton via a sulfur atom (—S—);

Alkenylamino: unsaturated, straight-chain or branched hydrocarbon radicals having 3 to 10 carbon atoms and a double bond in any position which is not adjacent to the hetero atom (as mentioned above) which are linked to the skeleton via an amino group (—NH—);

Alkenylcarbonyl: unsaturated, straight-chain or branched hydrocarbon radicals having 2 to 10 carbon atoms and a double bond in any position (as mentioned above) which are linked to the skeleton via a carbonyl group (—CO—);

Alkenyloxycarbonyl: straight-chain or branched alkenyloxy groups having 3 to 10 carbon atoms (as mentioned above) which are linked to the skeleton via a carbonyl group (—CO—);

Alkenylthiocarbonyl: straight-chain or branched alkenylthio groups having 3 to 10 carbon atoms (as mentioned above) which are linked to the skeleton via a carbonyl group (—CO—);

Alkenylaminocarbonyl: straight-chain or branched alkenylamino groups having 3 to 10 carbon atoms (as mentioned above) which are linked to the skeleton via a carbonyl group (—CO—);

Alkenylcarbonyloxy: unsaturated, straight-chain or branched hydrocarbon radicals having 2 to 10 carbon atoms and a double bond in any position (as mentioned above) which are linked to the skeleton via a carbonyloxy group (—CO$_2$—);

Alkenylcarbonylthio: unsaturated, straight-chain or branched hydrocarbon radicals having 2 to 10 carbon atoms and a double bond in any position (as mentioned above) which are linked to the skeleton via a carbonylthio group (—COS—);

Alkenylcarbonylamino: unsaturated, straight-chain or branched hydrocarbon radicals having 2 to 10 carbon atoms and a double bond in any position (as mentioned above) which are linked to the skeleton via a carbonylamino group (—CONH—);

Alkenylsulfonyl: unsaturated, straight-chain or branched hydrocarbon radicals having 2 to 10 carbon atoms and a double bond in any position (as mentioned above) which are linked to the skeleton via a sulfonylamino group (—SO$_2$—);

Alkenyloxysulfonyl: a straight-chain or branched alkenyloxy group having 3 to 10 carbon atoms (as mentioned above) which is linked to the skeleton via a sulfonyl group (—SO$_2$—);

Alkenylthiosulfonyl: a straight-chain or branched alkenylthio group having 3 to 10 carbon atoms (as mentioned above) which is linked to the skeleton via a sulfonyl group (—SO$_2$—);

Alkenylaminosulfonyl: a straight-chain or branched alkenylamino group having 3 to 10 carbon atoms (as mentioned above) which is linked to the skeleton via a sulfonyl group (—SO$_2$—);

Alkynyl: straight-chain or branched hydrocarbon groups having 2 to 4, 6, 8 or 10 carbon atoms and a triple bond in any position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Haloalkynyl: unsaturated, straight-chain or branched hydrocarbon radicals having 2 to 10 carbon atoms and a triple bond in any position (as mentioned above), it being possible for some or all of the hydrogen atoms in these groups to be replaced by halogen atoms as mentioned above, in particular fluorine, chlorine and bromine;

Alkynyloxy: unsaturated, straight-chain or branched hydrocarbon radicals having 3 to 10 carbon atoms and a triple bond in any position which is not adjacent to the hetero atom (as mentioned above) which are linked to the skeleton via an oxygen atom (—O—);

Haloalkynyloxy: unsaturated, straight-chain or branched alkynyloxy groups having 3 to 10 carbon atoms (as mentioned above), it being possible for some or all of the hydrogen atoms in these groups to be replaced by halogen atoms as mentioned above, in particular fluorine, chlorine and bromine;

Alkynylthio: unsaturated, straight-chain or branched hydrocarbon radicals having 3 to 10 carbon atoms and a triple bond in any position which is not adjacent to the hetero atom (as mentioned above) which are linked to the skeleton via a sulfur atom (—S—);

Alkynylamino: unsaturated, straight-chain or branched hydrocarbon radicals having 3 to 10 carbon atoms and a triple bond in any position which is not adjacent to the hetero atom (as mentioned above) which are linked to the skeleton via an amino group (—NH—);

Alkynylcarbonyl: unsaturated, straight-chain or branched hydrocarbon radicals having 2 to 10 carbon atoms and a triple bond in any position (as mentioned above) which are linked to the skeleton via a carbonyl group (—CO—);

Alkynyloxycarbonyl: straight-chain or branched alkynyloxy groups having 3 to 10 carbon atoms (as mentioned above) which are linked to the skeleton via a carbonyl group (—CO—);

Alkynylthiocarbonyl: straight-chain or branched alkynylthio groups having 3 to 10 carbon atoms (as mentioned above) which are linked to the skeleton via a carbonyl group (—CO—);

Alkynylaminocarbonyl: straight-chain or branched alkynylamino groups having 3 to 10 carbon atoms (as mentioned above) which are linked to the skeleton via a carbonyl group (—CO—);

Alkynylcarbonyloxy: unsaturated, straight-chain or branched hydrocarbon radicals having 2 to 10 carbon atoms and a triple bond in any position (as mentioned above) which are linked to the skeleton via a carbonyloxy group (—CO$_2$—);

Alkynylcarbonylthio: unsaturated, straight-chain or branched hydrocarbon radicals having 2 to 10 carbon atoms and a triple bond in any position (as mentioned above) which are linked to the skeleton via a carbonylthio group (—COS—);

Alkynylcarbonylamino: unsaturated, straight-chain or branched hydrocarbon radicals having 2 to 10 carbon atoms and a triple bond in any position (as mentioned above) which are linked to the skeleton via a carbonylamino group (—CONH—);

Alkynylsulfonyl: unsaturated, straight-chain or branched hydrocarbon radicals having 2 to 10 carbon atoms and a triple bond in any position (as mentioned above) which are linked to the skeleton via a sulfonyl group (—SO$_2$—);

Alkynyloxysulfonyl: a straight-chain or branched alkynyloxy group having 3 to 10 carbon atoms (as mentioned above) which is linked to the skeleton via a sulfonyl group (—SO$_2$—);

Alkynylthiosulfonyl: a straight-chain or branched alkynylthio group having 3 to 10 carbon atoms (as mentioned above) which are linked to the skeleton via a sulfonyl group (—SO$_2$—);

Alkynylaminosulfonyl: a straight-chain or branched alkynylamino group having 3 to 10 carbon atoms (as mentioned above) which is linked to the skeleton via a sulfonyl group (—SO$_2$—);

Cycloalkyl: monocyclic, saturated hydrocarbon groups having 3 to 6, 8, 10 or 12 carbon ring members, eg. $C_3$–$C_8$-cycloalkyl, such as cyclopropyl, cyclobutyl, cyclopentyl, cyclohexyl, cycloheptyl and cyclooctyl;

Cycloalkoxy: monocyclic, saturated hydrocarbon groups having 3 to 12 carbon ring members (as mentioned above) which are linked to the skeleton via an oxygen atom (—O—);

Cycloalkylthio: monocyclic, saturated hydrocarbon groups having 3 to 12 carbon ring members (as mentioned above) which are linked to the skeleton via a sulfur atom (—S—);

Cycloalkylamino: monocyclic, saturated hydrocarbon groups having 3 to 12 carbon ring members (as mentioned above) which are linked to the skeleton via an amino group (—NH—);

Cycloalkylcarbonyl: monocyclic, saturated hydrocarbon groups having 3 to 12 carbon ring members (as mentioned above) which are linked to the skeleton via a carbonyl group (—CO—);

Cycloalkoxycarbonyl: a monocyclic cycloalkoxy group having 3 to 12 carbon ring members (as mentioned above) which is linked to the skeleton via a carbonyl group (—CO—);

Cycloalkylthiocarbonyl: a monocyclic cycloalkylthio group having 3 to 12 carbon ring members (as mentioned above) which is linked to the skeleton via a carbonyl group (—CO—);

Cycloalkylaminocarbonyl: a monocyclic cycloalkylamino group having 3 to 12 carbon ring members (as mentioned above) which is linked to the skeleton via a carbonyl group (—CO—);

Cycloalkylcarbonyloxy: monocyclic, saturated hydrocarbon groups having 3 to 12 carbon ring members (as mentioned above) which are linked to the skeleton via a carbonyloxy group (—CO$_2$—);

Cycloalkylcarbonylthio: monocyclic, saturated hydrocarbon groups having 3 to 12 carbon ring members (as mentioned above) which are linked to the skeleton via a carbonylthio group (—COS—);

Cycloalkylcarbonylamino: monocyclic, saturated hydrocarbon groups having 3 to 12 carbon ring members (as mentioned above) which are linked to the skeleton via a carbonylamino group (—CONH—);

Cycloalkylsulfonyl: monocyclic, saturated hydrocarbon groups having 3 to 12 carbon ring members (as mentioned above) which are linked to the skeleton via a sulfonyl group (—SO$_2$—);

Cycloalkoxysulfonyl: a monocyclic cycloalkoxy group having 3 to 12 carbon ring members (as mentioned above) which is linked to the skeleton via a sulfonyl group (—SO$_2$—);

Cycloalkylthiosulfonyl: a monocyclic cycloalkylthio group having 3 to 12 carbon ring members (as mentioned above) which is linked to the skeleton via a sulfonyl group (—SO$_2$—);

Cycloalkylaminosulfonyl: a monocyclic cycloalkylamino group having 3 to 12 carbon ring members (as mentioned above) which is linked to the skeleton via a sulfonyl group (—SO$_2$—);

saturated or partially unsaturated cyclic radical, which, besides carbon atoms, can contain, as ring members, hetero atoms from the group consisting of oxygen, sulfur or nitrogen: cycloalkyl having 3 to 12 carbon ring members as mentioned above or 5- or 6-membered heterocycles (heterocyclyl) containing, besides carbon ring members, one to three nitrogen atoms and/or an oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl;

Heterocyclyloxy: a 5- or 6-membered heterocycle (as mentioned above) which is linked to the skeleton via an oxygen atom (—O—);

Heterocyclylthio: a 5- or 6-membered heterocycle (as mentioned above) which is linked to the skeleton via a sulfur atom (—S—);

Heterocyclylamino: a 5- or 6-membered heterocycle (as mentioned above) which is linked to the skeleton via an amino group (—NH—);

Heterocyclylcarbonyl: a 5- or 6-membered heterocycle (as mentioned above) which is linked to the skeleton via a carbonyl group (—CO—);

Heterocyclyloxycarbonyl: a heterocyclyloxy group (as mentioned above) which is linked to the skeleton via a carbonyl group (—CO—);

Heterocyclylthiocarbonyl: a heterocyclylthio group (as mentioned above) which is linked to the skeleton via a carbonyl group (—CO—);

Heterocyclylaminocarbonyl: a 5- or 6-membered heterocycle (as mentioned above) which is linked to the skeleton via an aminocarbonyl group (—NHCO—);

Heterocyclylcarbonyloxy: a 5- or 6-membered heterocycle (as mentioned above) which is linked to the skeleton via a carbonyloxy group (—CO$_2$—);

Heterocyclylcarbonylthio: a 5- or 6-membered heterocycle (as mentioned above) which is linked to the skeleton via a carbonylthio group (—COS—);

Heterocyclylcarbonylamino: a 5- or 6-membered heterocycle (as mentioned above) which is linked to the skeleton via a carbonylamino group (—CONH—);

Heterocyclylsulfonyl: a 5- or 6-membered heterocycle (as mentioned above) which is linked to the skeleton via a sulfonyl group (—SO$_2$—);

Aryloxysulfonyl: a heterocyclyloxy group (as mentioned above) which is linked to the skeleton via a sulfonyl group (—SO$_2$—);

Heterocyclylthiosulfonyl: a heterocyclylthio group (as mentioned above) which is linked to the skeleton via a sulfonyl group (—SO$_2$—);

Heterocyclylaminosulfonyl: a heterocyclylamino group (as mentioned above) which is linked to the skeleton via a sulfonyl group (—SO$_2$—);

Aryl: a mono- to trinuclear aromatic ring system containing 6 to 14 carbon ring members, eg. phenyl, naphthyl and anthracenyl;

Aryloxy: a mono- to trinuclear aromatic ring system (as mentioned above) which is linked to the skeleton via an oxygen atom (—O—);

Arylthio: a mono- to trinuclear aromatic ring system (as mentioned above) which is linked to the skeleton via a sulphur atom (—S—);

Arylamino: a mono- to trinuclear aromatic ring system (as mentioned above) which is linked to the skeleton via an amino group (—NH—);

Arylcarbonyl: a mono- to trinuclear aromatic ring system (as mentioned above) which is linked to the skeleton via a carbonyl group (—CO—);

Aryloxycarbonyl: a mono- to trinuclear aryloxy group (as mentioned above) which is linked to the skeleton via a carbonyl group (—CO—);

Arylthiocarbonyl: a mono- to trinuclear arylthio group (as mentioned above) which is linked to the skeleton via a carbonyl group (—CO—);

Arylaminocarbonyl: a mono- to trinuclear arylamino group (as mentioned above) which is linked to the skeleton via a carbonyl group (—CO—);

Arylcarbonyloxy: a mono- to trinuclear aromatic ring system (as mentioned above) which is linked to the skeleton via a carbonyloxy group (—CO$_2$—);

Arylcarbonylthio: a mono- to trinuclear aromatic ring system (as mentioned above) which is linked to the skeleton via a carbonylthio group (—COS—);

Arylcarbonylamino: a mono- to trinuclear aromatic ring system (as mentioned above) which is linked to the skeleton via a carbonylamino group (—CONH—);

Arylsulfonyl: a mono- to trinuclear aromatic ring system (as mentioned above) which is linked to the skeleton via a sulfonyl group (—SO$_2$—);

Aryloxysulfonyl: a mono- to trinuclear aryloxy group (as mentioned above) which is linked to the skeleton via a sulfonyl group (—SO$_2$—);

Arylthiosulfonyl: a mono- to trinuclear arylthio group (as mentioned above) which is linked to the skeleton via a sulfonyl group (—SO$_2$—);

Arylaminosulfonyl: a mono- to trinuclear arylamino group (as mentioned above) which is linked to the skeleton via a sulfonyl group (—SO$_2$—);

aromatic ring system, which, besides carbon ring members, can contain hetero atoms from the group consisting of oxygen, sulfur and nitrogen: aryl as mentioned above or mono- or binuclear hetaryl, eg.

5-membered hetaryl, containing one to four nitrogen atoms or one to three nitrogen atoms and a sulfur or oxygen atom: 5-membered hetaryl ring groups, which, besides carbon atoms, may contain, as ring members, one to four nitrogen atoms or one to three nitrogen atoms and a sulfur or oxygen atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered hetaryl, containing one to three nitrogen atoms or a nitrogen atom and an oxvgen of sulfur atom: 5-membered hetaryl ring groups, which, besides carbon atoms, may contain, as ring members, one to four nitrogen atoms or one to three nitrogen atoms and a sulfur or oxygen atom and in which two adjacent carbon ring members or a nitrogen and an adjacent carbon ring members can be bridged by a buta-1,3-diene- 1,4-diyl group;

5-membered hetarvl, linked via nitrogen and containing one to four nitrogen atoms, or benzo-fused 5-membered hetaryl, linked via nitrogen and containing one to three nitrogen atoms: 5-membered hetaryl ring groups which, besides carbon atoms, may contain, as ring members, one to four nitrogen atoms, or one to three nitrogen atoms, and in which two adjacent carbon ring members or a nitrogen and an adjacent carbon ring member can be bridged by a buta-1,3-diene-1,4-diyl group, these rings being linked to the skeleton via one of the nitrogen ring members;

6-membered hetaryl, containing one to three, or one to four, nitrogen atoms: 6-membered hetaryl ring groups which, besides carbon atoms, may contain, as ring members, one to three, or one to four, nitrogen atoms, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Hetaryloxy: a mono- to trinuclear heteroaromatic ring system (as mentioned above) which is linked to the skeleton via an oxygen atom (—O—);

Hetarylthio: a mono- to trinuclear heteroaromatic ring system (as mentioned above) which is linked to the skeleton via a sulfur atom (—S—);

Hetarylamino: a mono- to trinuclear heteroaromatic ring system (as mentioned above) which is linked to the skeleton via an amino group (—NH—);

Hetarylcarbonyl: a mono- to trinuclear heteroaromatic ring system (as mentioned above) which is linked to the skeleton via a carbonyl group (—CO—);

Hetaryloxycarbonyl: a mono- to trinuclear hetaryloxy group (as mentioned above) which is linked to the skeleton via a carbonyl group (—CO—);

Hetarylthiocarbonyl: a mono- to trinuclear hetarylthio group (as mentioned above) which is linked to the skeleton via a carbonyl group (—CO—);

Hetarylaminocarbonyl: a mono- to trinuclear hetarylamino group (as mentioned above) which is linked to the skeleton via a carbonyl group (—CO—);

Hetarylcarbonyloxy: a mono- to trinuclear heteroaromatic ring system (as mentioned above) which is linked to the skeleton via a carbonyloxy group (—CO$_2$—);

Hetarylcarbonylthio: a mono- to trinuclear heteroaromatic ring system (as mentioned above) which is linked to the skeleton via a carbonylthio group (—COS—);

Hetarylcarbonylamino: a mono- to trinuclear heteroaromatic ring system (as mentioned above) which is linked to the skeleton via carbonylamino group (—CONH—);

Hetarylsulfonyl: a mono- to trinuclear heteroaromatic ring system (as mentioned above) which is linked to the skeleton via a sulfonyl group (—SO$_2$—);

Hetaryloxysulfonyl: a mono- to trinuclear hetaryloxy group (as mentioned above) which is linked to the skeleton via a sulfonyl group (—SO$_2$—);

Hetarylthiosulfonyl: a mono- to trinuclear hetarylthio group (as mentioned above) which is linked to the skeleton via a sulfonyl group (—SO$_2$—);

Hetarylaminosulfonyl: a mono- to trinuclear hetarylamino group (as mentioned above) which is linked to the skeleton via a sulfonyl group (—SO$_2$—);

Alkylene: divalent unbranched chains of 3 to 5 $CH_2$ groups, eg. $CH_2$, $CH_2CH_2$, $CH_2CH_2CH_2$, $CH_2CH_2CH_2CH_2$ and $CH_2CH_2CH_2CH_2CH_2$;

Oxyalkylene: divalent unbranched chains of 2 to 4 $CH_2$ groups, one valency being linked to the skeleton via an oxygen atom, eg. $OCH_2CH_2$, $OCH_2CH_2CH_2$ and $OCH_2CH_2CH_2CH_2$;

Oxyalkyleneoxy: divalent unbranched chains of 1 to 3 $CH_2$ groups, both valencies being linked to the skeleton via an oxygen atom, eg. $OCH_2O$, $OCH_2CH_2O$ and $OCH_2CH_2CH_2O$;

Alkenylene: divalent unbranched chains of 1 to 3 $CH_2$ groups and one CH=CH group in any position, eg. CH=CHCH$_2$, CH$_2$CH=CHCH$_2$, CH=CHCH$_2$CH$_2$, CH$_2$CH=CHCH$_2$CH$_2$ and CH=CHCH$_2$CH$_2$CH$_2$;

Oxyalkenylene: divalent unbranched chains of 0 to 2 $CH_2$ groups and one CH=CH group in any position, one valency being linked to the skeleton via an oxygen atom, eg. OCH=CH, OCH=CHCH$_2$, OCH$_2$CH=CH, OCH$_2$CH=CHCH$_2$, OCH=CHCH$_2$CH$_2$ and OCH$_2$CH$_2$—CH=CH;

Oxyalkenyleneoxy: divalent unbranched chains of 0 to 2 $CH_2$ groups and one CH=CH group in any position, both valencies being linked to the skeleton via an oxygen atom, eg. OCH=CHO, OCH=CHCH$_2$O, OCH$_2$CH=CHCH$_2$O and OCH=CHCH$_2$CH$_2$O;

organic radical: unsubstituted or substituted alkyl, alkenyl, alkynyl, cycloalkyl, heterocyclyl, aryl or hetaryl.

The term "unsubstituted or substituted" relating to alkyl, alkenyl and alkynyl groups is intended to express that these groups may be partially or fully halogenated [ie. some or all of the hydrogen atoms in these groups may be replaced by identical or different halogen atoms as mentioned above (preferably fluorine, chlorine or bromine)] and/or can have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms;

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N- alkylamino, unsubstituted or substituted by customary groups, the aryl radicals preferably containing 6 to 10 ring members, in particular 6 ring members (phenyl), the hetaryl radicals containing, in particular, 5 or 6 ring members and the alkyl groups in these radicals preferably containing 1 to 6 carbon atoms, in particular 1 to 4 carbon atoms.

The term "ubsubstituted or substituted" when relating to the cyclic (saturated, unsaturated or aromatic) groups is intended to express that these groups may be partially or fully halogenated [ie. some or all of the hydrogen atoms in these groups may be replaced by identical or different halogen atoms as mentioned above (preferably fluorine, chlorine or bromine, in particular fluorine or chlorine)] and/or can have attached to them one to four (in particular one to three) of the following radicals:

cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms, and the alkenyl or alkynyl groups mentioned in these radicals containing 2 to 8, preferably 2 to 6, in particular 2 to 4, carbon atoms;

and/or one to three (in particular one) of the following radicals:

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals preferably containing 1 to 6 carbon atoms, in particular 1 to 4 carbon atoms;

and/or one or two (in particular one) of the following radicals:

formyl, $CR^{iii}$=$NOR^{iv}$ [where $R^{iii}$ is hydrogen, alkyl, cycloalkyl and aryl and $R^{iv}$ is alkyl, alkenyl, haloalkenyl, alkynyl and arylalkyl (the abovementioned alkyl groups preferably containing 1 to 6 carbon atoms, in particular 1 to 4 carbon atoms, the abovementioned cycloalkyl groups, alkenyl groups and alkynyl groups preferably containing 3 to 8, in particular 3 to 6, carbon atoms) and aryl is in particular phenyl which is unsubstituted or can be substituted by customary groups] or $NR^v$—CO—D—$R^{vi}$ [where $R^v$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl, $R^{vi}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl and D is a direct linkage, oxygen or nitrogen, it being possible for the nitrogen to have attached to it one of the groups mentioned under $R^{vi}$], and/or where two adjacent C atoms of the cyclic systems can have attached to them a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadienediyl group, it being possible for these bridges, in turn, to be partially or fully halogenated and/or to have attached to them one to three, in particular one or two of the following radicals:

$C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups are to be understood as meaning in particular the following substituents: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

Especially preferred compounds I are those where Q is $C(CO_2CH_3)$=$CHCH_3$, $C(CO_2CH_3)$=$CHOCH_3$, $C(CO_2CH_3)$=$NOCH_3$, $C(CONHCH_3)$=$NOCH_3$ or $N(OCH_3)$—$CO_2CH_3$.

Other especially preferred compounds of the formula I are those where $R^1$ is hydrogen or one of the following groups: unsubstituted or substituted alkyl, alkenyl, alkynyl, cycloalkyl, heterocyclyl, aryl or hetaryl.

Moreover, especially preferred compounds I are those where $R^1$ is unsubstituted or substituted $C_1$–$C_6$-alkyl.

Equally, especially preferred compounds I are those where $R^1$ is unsubstituted or substituted $C_3$–$C_6$-alkenyl.

Besides, especially preferred compounds I are those where $R^1$ is unsubstituted or substituted $C_3$–$C_6$-alkynyl.

Other particularly preferred compounds I are those where $R^1$ is $C_1$–$C_6$-haloalkyl.

Moreover, especially preferred compounds I are those where $R^1$ is $C_3$–$C_6$-haloalkenyl.

Equally, especially preferred compounds I are those where $R^1$ is aryl-$C_1$–$C_2$-alkyl, it being possible for the aryl radical to be unsubstituted or substituted.

Especially preferred compounds I are those where $R^1$ is aryl-$C_1$–$C_2$-alkyl, it being possible for the aryl radical to be partially or fully halogenated and/or to have attached to it one to three of the following groups: $C_1$–$C_4$-alkyl, $C_1$–$C_4$-haloalkyl and $C_1$–$C_4$-alkoxy.

Besides, especially preferred compounds I are those where $R^1$ is $C_3$–$C_6$-cycloalkyl-$C_1$–$C_2$-alkyl, it being possible for the cycloalkyl radical to be unsubstituted or substituted.

Especially preferred compounds I are those where $R^1$ is $C_3$–$C_6$-cycloalkyl-$C_1$–$C_2$-alkyl, it being possible for the cycloalkyl radical to be partially or fully halogenated and/or to have attached to it one to three $C_1$–$C_4$-alkyl groups.

Furthermore, especially preferred compounds I are those where $R^1$ is hetaryl-$C_1$–$C_2$-alkyl, it being possible for the hetaryl radical to be unsubstituted or substituted.

Especially preferred compounds I are those where $R^1$ is hetaryl-$C_1$–$C_2$-alkyl, it being possible for the hetaryl radical to be partially or fully halogenated and/or to have attached to it one to three of the following groups: $C_1$–$C_4$-alkyl, $C_1$–$C_4$-haloalkyl and $C_1$–$C_4$-alkoxy.

Moreover, especially preferred compounds of the formula I are those where $R^2$ is hydrogen or one of the following groups: unsubstituted or substituted alkyl, alkenyl, alkynyl, cycloalkyl, heterocyclyl, aryl or hetaryl, it being possible for these groups to be linked to the skeleton directly (by a carbon atom) or by an oxygen, sulfur or nitrogen atom.

Particularly preferred compounds I are those where $R^2$ is unsubstituted or substituted $C_1$–$C_6$-alkyl.

Moreover, especially preferred compounds I are those where $R^2$ is unsubstituted or substituted $C_2$–$C_6$-alkenyl.

Equally, especially preferred compounds I are those where $R^2$ is unsubstituted or substituted $C_2$–$C_6$-alkynyl.

Besides, especially preferred compounds I are those where $R^2$ is $C_3$–$C_6$-cycloalkyl.

Other particularly preferred compounds I are those where $R^2$ is aryl.

Moreover, especially preferred compounds I are those where $R^2$ is hetaryl.

Moreover, especially preferred compounds I are those where $R^3$ is hydrogen, halogen, $C_1$–$C_3$-alkyl or $C_1$–$C_2$-haloalkyl, in particular hydrogen, methyl, fluorine, chlorine, ethyl, isopropyl and trifluoromethyl.

Particularly preferred compounds I are those where $R^3$ is hydrogen.

Furthermore, especially preferred compounds I are those where $R^3$ is halogen, in particular fluorine, chlorine and bromine.

Equally, especially preferred compounds I are those where $R^3$ is methyl.

Besides, especially preferred compounds I are those where $R^3$ is $C_1$-haloalkyl, in particular trifluoromethyl.

Furthermore, preferred compounds I are those where $R^4$ is hydrogen.

Besides, preferred compounds I are those where $R^4$ is halogen, in particular fluorine, chlorine and bromine.

Moreover, especially preferred compounds I are those where $R^4$ is $C_1$–$C_2$-alkyl.

Equally, especially preferred compounds I are those where $R^4$ is $C_1$–$C_2$-alkoxy.

Besides, especially preferred compounds I are those where $R^4$ is cyano.

Other particularly preferred compounds I are those where $R^4$ is nitro.

Furthermore, especially preferred compounds I are those where y is 0, 1, 2 or 3, it being possible for the radicals $R^5$ to be different if y is 2 or 3.

Especially preferred compounds I are those where y is 0 or 1.

Moreover, especially preferred compounds I are those where $R^5$ is cyano, halogen, $C_1$–$C_3$-alkyl, $C_1$–$C_2$-halogenalkyl or $C_1$–$C_3$-alkoxy, in particular cyano, fluorine, chlorine, methyl, ethyl, isopropyl, trifluoromethyl, methoxy or ethoxy.

Particularly preferred compounds I are those where $R^5$ is methyl.

Moreover, especially preferred compounds I are those where $R^5$ is methoxy.

Equally, especially preferred compounds I are those where $R^5$ is fluorine.

Besides, especially preferred compounds I where $R^5$ is chlorine.

Other compounds I which are particularly preferred are those where $R^5$ is trifluoromethyl.

Moreover, especially preferred compounds I are those where $R^5$ is $OCH_2O$.

Particularly preferred with a view to their use are the compounds I compiled in the tables below. Moreover the groups mentioned in the tables for one substituent are, considered on their own, an especially preferred embodiment of the substituent in question, independently of the combination in which they are mentioned.

Table 1

Componds of the general formula IA.1 where $R^2$ is methyl, $R^3$ is hydrogen, $R^4$ is hydrogen, $R^5_y$ is hydrogen and $R^1$ for each compound corresponds to a group of Table A.

IA.1

Table 2

Componds of the general formula IA.2 where $R^2$ is methyl, $R^3$ is hydrogen, $R^4$ is hydrogen, $R^5_y$ is hydrogen and $R^1$ for each compound corresponds to a group of Table A.

IA.2

Table 3

Componds of the general formula IA.3, where $R^2$ is methyl, $R^3$ is hydrogen, $R^4$ is hydrogen, $R^5_y$ is hydrogen and $R^1$ for each compound corresponds to a group of Table A.

IA.3

Table 4

Componds of the general formula IA.4, where $R^2$ is methyl, $R^3$ is hydrogen, $R^4$ is hydrogen, $R^5_y$ is hydrogen and $R^1$ for each compound corresponds to a group of Table A.

IA.4

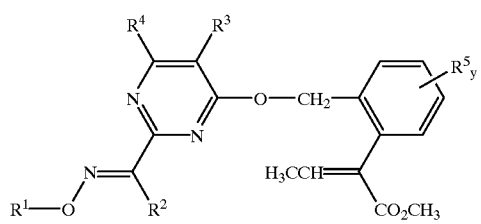

Table 5

Componds of the general formula IA.5, where $R^2$ is methyl, $R^3$ is hydrogen, $R^4$ is hydrogen, $R^5_y$ is hydrogen and $R^1$ for each compound corresponds to a group of Table A.

IA.5

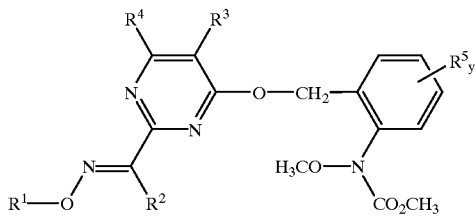

Table 6

Componds of the general formula IA.6, where $R^2$ is methyl, $R^3$ is hydrogen, $R^4$ is hydrogen, $R^5_y$ is hydrogen and $R^1$ for each compound corresponds to a group of Table A.

IA.6

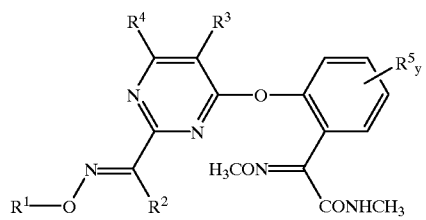

Table 7

Componds of the general formula IA.7, where $R^2$ is methyl, $R^3$ is hydrogen, $R^4$ is hydrogen, $R^5_y$ is hydrogen and $R^1$ for each compound corresponds to a group of Table A.

IA.7

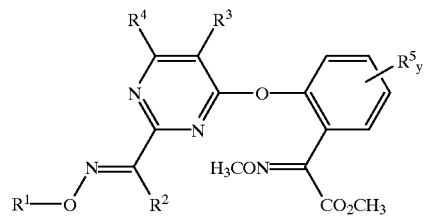

Table 8

Componds of the general formula IA.8, where $R^2$ is methyl, $R^3$ is hydrogen, $R^4$ is hydrogen, $R^5_y$ is hydrogen and $R^1$ for each compound corresponds to a group of Table A.

IA.8

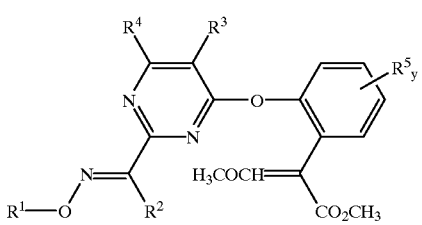

Table 9

Componds of the general formula IA.9, where $R^2$ is methyl, $R^3$ is hydrogen, $R^4$ is hydrogen, $R^5_y$ is hydrogen and $R^1$ for each compound corresponds to a group of Table A.

IA.9

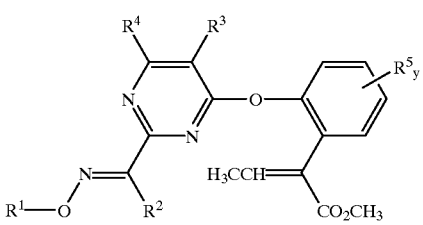

Table 10

Componds of the general formula IA.10, where $R^2$ is methyl, $R^3$ is hydrogen, $R^4$ is hydrogen, $R^5_y$ is hydrogen and $R^1$ for each compound corresponds to a group of Table A.

IA.10

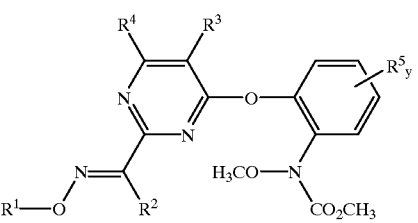

Table 11

Componds of the general formula IB.1, where $R^2$ is methyl, $R^3$ is hydrogen, $R^4$ is hydrogen, $R^5_y$ is hydrogen and $R^1$ for each compound corresponds to a group of Table A.

IB.1

[Structure IB.1]

Table 12

Componds of the general formula IB.2, where $R^2$ is methyl, $R^3$ is hydrogen, $R^4$ is hydrogen, $R^5_y$ is hydrogen and $R^1$ for each compound corresponds to a group of Table A.

IB.2

[Structure IB.2]

Table 13

Componds of the general formula IB.3, where $R^2$ is methyl, $R^3$ is hydrogen, $R^4$ is hydrogen, $R^5_y$ is hydrogen and $R^1$ for each compound corresponds to a group of Table A.

IB.3

[Structure IB.3]

Table 14

Componds of the general formula IB.4, where $R^2$ is methyl, $R^3$ is hydrogen, $R^4$ is hydrogen, $R^5_y$ is hydrogen and $R^1$ for each compound corresponds to a group of Table A.

IB.4

[Structure IB.4]

Table 15

Componds of the general formula IB.5, where $R^2$ is methyl, $R^3$ is hydrogen, $R^4$ is hydrogen, $R^5_y$ is hydrogen and $R^1$ for each compound corresponds to a group of Table A.

IB.5

[Structure IB.5]

Table 16

Componds of the general formula IB.6, where $R^2$ is methyl, $R^3$ is hydrogen, $R^4$ is hydrogen, $R^5_y$ is hydrogen and $R^1$ for each compound corresponds to a group of Table A.

IB.6

[Structure IB.6]

Table 17

Componds of the general formula IB.7, where $R^2$ is methyl, $R^3$ is hydrogen, $R^4$ is hydrogen, $R^5_y$ is hydrogen and $R^1$ for each compound corresponds to a group of Table A.

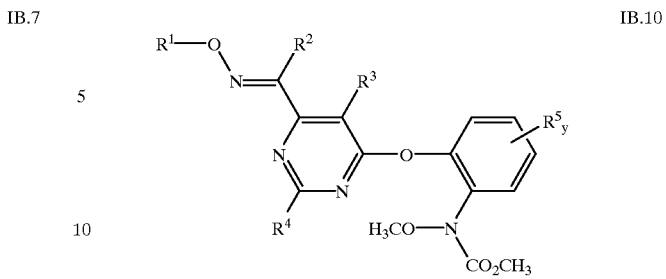

IB.7

Table 18

Componds of the general formula IB.8, where $R^2$ is methyl, $R^3$ is hydrogen, $R^4$ is hydrogen, $R^5_y$ is hydrogen and $R^1$ for each compound corresponds to a group of Table A.

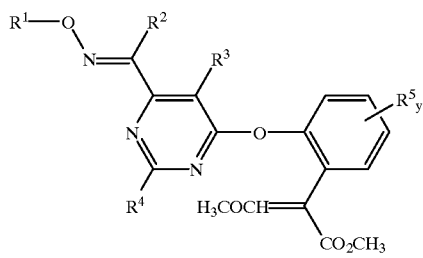

IB.8

Table 19

Componds of the general formula IB.9, where $R^2$ is methyl, $R^3$ is hydrogen, $R^4$ is hydrogen, $R^5_y$ is hydrogen and $R^1$ for each compound corresponds to a group of Table A.

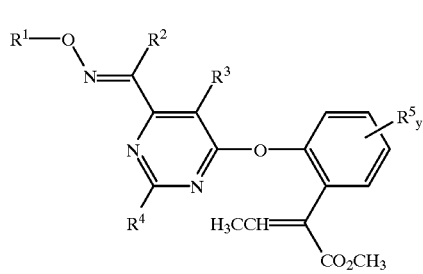

IB.9

Table 20

Componds of the general formula IB.10, where $R^2$ is methyl, $R^3$ is hydrogen, $R^4$ is hydrogen, $R^5_y$ is hydrogen and $R^1$ for each compound corresponds to a group of Table A.

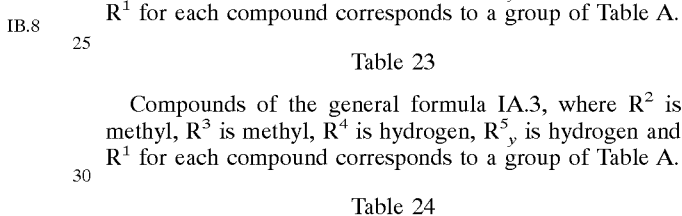

IB.10

Table 21

Componds of the general formula IA.1, where $R^2$ is methyl, $R^3$ is hydrogen, $R^4$ is hydrogen, $R^5_y$ is hydrogen and $R^1$ for each compound corresponds to a group of Table A.

Table 22

Compounds of the general formula IA.2, where $R^2$ is methyl, $R^3$ is methyl, $R^4$ is hydrogen, $R^5_y$ is hydrogen and $R^1$ for each compound corresponds to a group of Table A.

Table 23

Compounds of the general formula IA.3, where $R^2$ is methyl, $R^3$ is methyl, $R^4$ is hydrogen, $R^5_y$ is hydrogen and $R^1$ for each compound corresponds to a group of Table A.

Table 24

Compounds of the general formula IA.4, where $R^2$ is methyl, $R^3$ is methyl, $R^4$ is hydrogen, $R^5_y$ is hydrogen and $R^1$ for each compound corresponds to a group of Table A.

Table 25

Compounds of the general formula IA.5, where $R^2$ is methyl, $R^3$ is methyl, $R^4$ is hydrogen, $R^5_y$ is hydrogen and $R^1$ for each compound corresponds to a group of Table A.

Table 26

Compounds of the general formula IA.6, where $R^2$ is methyl, $R^3$ is methyl, $R^4$ is hydrogen, $R^5_y$ is hydrogen and $R^1$ for each compound corresponds to a group of Table A.

Table 27

Compounds of the general formula IA.7, where $R^2$ is methyl, $R^3$ is methyl, $R^4$ is hydrogen, $R^5_y$ is hydrogen and $R^1$ for each compound corresponds to a group of Table A.

Table 28

Compounds of the general formula IA.8, where $R^2$ is methyl, $R^3$ is methyl, $R^4$ is hydrogen, $R^5_y$ is hydrogen and $R^1$ for each compound corresponds to a group of Table A.

Table 29

Compounds of the general formula IA.9, where $R^2$ is methyl, $R^3$ is methyl, $R^4$ is hydrogen, $R^5_y$ is hydrogen and $R^1$ for each compound corresponds to a group of Table A.

Table 30

Compounds of the general formula IA.10, where $R^2$ is methyl, $R^3$ is methyl, $R^4$ is hydrogen, $R^5_y$ is hydrogen and $R^1$ for each compound corresponds to a group of Table A.

Table 31

Compounds of the general formula IA.1, where $R^2$ is methyl, $R^3$ is chlorine, $R^4$ is hydrogen, $R^5_y$ is hydrogen, $R^1$ for each compound corresponds to a group of Table A.

Table 32

Compounds of the general formula IA.2, where $R^2$ is methyl, $R^3$ is chlorine, $R^4$ is hydrogen, $R^5_y$ is hydrogen and $R^1$ for each compound corresponds to a group of Table A.

Table 33

Compounds of the general formula IA.3, where $R^2$ is methyl, $R^3$ is chlorine, $R^4$ is hydrogen, $R^5_y$ is hydrogen and $R^1$ for each compound corresponds to a group of Table A.

Table 34

Compounds of the general formula IA.4, where $R^2$ is methyl, $R^3$ is chlorine, $R^4$ is hydrogen, $R^5_y$ is hydrogen and $R^1$ for each compound corresponds to a group of Table A.

Table 35

Compounds of the general formula IA.5, where $R^2$ is methyl, $R^3$ is chlorine, $R^4$ is hydrogen, $R^5_y$ is hydrogen and $R^1$ for each compound corresponds to a group of Table A.

Table 36

Compounds of the general formula IA.6, where $R^2$ is methyl, $R^3$ is chlorine, $R^4$ is hydrogen, $R^5_y$ is hydrogen and $R^1$ for each compound corresponds to a group of Table A.

Table 37

Compounds of the general formula IA.7, where $R^2$ is methyl, $R^3$ is chlorine, $R^4$ is hydrogen, $R^5_y$ is hydrogen and $R^1$ for each compound corresponds to a group of Table A.

Table 38

Compounds of the general formula IA.8, where $R^2$ is methyl, $R^3$ is chlorine, $R^4$ is hydrogen, $R^5_y$ is hydrogen and $R^1$ for each compound corresponds to a group of Table A.

Table 39

Compounds of the general formula IA.9, where $R^2$ is methyl, $R^3$ is chlorine, $R^4$ is hydrogen, $R^5_y$ is hydrogen and $R^1$ for each compound corresponds to a group of Table A.

Table 40

Compounds of the general formula IA.10, where $R^2$ is methyl, $R^3$ is chlorine, $R^4$ is hydrogen, $R^5_y$ is hydrogen and $R^1$ for each compound corresponds to a group of Table A.

Table 41

Compounds of the general formula IA.1, where $R^2$ is methyl, $R^3$ is fluorine, $R^4$ is hydrogen, $R^5_y$ is hydrogen and $R^1$ for each compound corresponds to a group of Table A.

Table 42

Compounds of the general formula IA.2, where $R^2$ is methyl, $R^3$ is fluorine, $R^4$ is hydrogen, $R^5_y$ is hydrogen and $R^1$ for each compound corresponds to a group of Table A.

Table 43

Compounds of the general formula IA.3, where $R^2$ is methyl, $R^3$ is fluorine, $R^4$ is hydrogen, $R^5_y$ is hydrogen and $R^1$ for each compound corresponds to a group of Table A.

Table 44

Compounds of the general formula IA.4, where $R^2$ is methyl, $R^3$ is fluorine, $R^4$ is hydrogen, $R^5_y$ is hydrogen and $R^1$ for each compound corresponds to a group of Table A.

Table 45

Compounds of the general formula IA.5, where $R^2$ is methyl, $R^3$ is fluorine, $R^4$ is hydrogen, $R^5_y$ is hydrogen and $R^1$ for each compound corresponds to a group of Table A.

Table 46

Compounds of the general formula IA.6, where $R^2$ is methyl, $R^3$ is fluorine, $R^4$ is hydrogen, $R^5_y$ is hydrogen and $R^1$ for each compound corresponds to a group of Table A.

Table 47

Compounds of the general formula IA.7, where $R^2$ is methyl, $R^3$ is fluorine, $R^4$ is hydrogen, $R^5_y$ is hydrogen and $R^1$ for each compound corresponds to a group of Table A.

Table 48

Compounds of the general formula IA.8, where $R^2$ is methyl, $R^3$ is fluorine, $R^4$ is hydrogen, $R^5_y$ is hydrogen and $R^1$ for each compound corresponds to a group of Table A.

Table 49

Compounds of the general formula IA.9, where $R^2$ is methyl, $R^3$ is fluorine, $R^4$ is hydrogen, $R^5_y$ is hydrogen and $R^1$ for each compound corresponds to a group of Table A.

Table 50

Compounds of the general formula IA.10, where $R^2$ is methyl, $R^3$ is fluorine, $R^4$ is hydrogen, $R^5_y$ is hydrogen and $R^1$ for each compound corresponds to a group of Table A.

Table 51

Compounds of the general formula IA.1, where $R^2$ is methyl, $R^3$ is bromine, $R^4$ is hydrogen, $R^5_y$ is hydrogen and $R^1$ for each compound corresponds to a group of Table A.

Table 52

Compounds of the general formula IA.2, where $R^2$ is methyl, $R^3$ is bromine, $R^4$ is hydrogen, $R^5_y$ is hydrogen and RI for each compound corresponds to a group of Table A.

Table 53

Compounds of the general formula IA.3, where $R^2$ is methyl, $R^3$ is bromine, $R^4$ is hydrogen, $R^5_y$ is hydrogen and $R^1$ for each compound corresponds to a group of Table A.

Table 54

Compounds of the general formula IA.4, where $R^2$ is methyl, $R^3$ is bromine, $R^4$ is hydrogen, $R^5_y$ is hydrogen and $R^1$ for each compound corresponds to a group of Table A.

Table 55

Compounds of the general formula IA.5, where $R^2$ is methyl, $R^3$ is bromine, $R^4$ is hydrogen, $R^5_y$ is hydrogen and $R^1$ for each compound corresponds to a group of Table A.

Table 56

Compounds of the general formula IA.6, where $R^2$ is methyl, $R^3$ is bromine, $R^4$ is hydrogen, $R^5_y$ is hydrogen and $R^1$ for each compound corresponds to a group of Table A.

Table 57

Compounds of the general formula IA.7, where $R^2$ is methyl, $R^3$ is bromine, $R^4$ is hydrogen, $R^5_y$ is hydrogen and $R^1$ for each compound corresponds to a group of Table A.

Table 58

Compounds of the general formula IA.8, where $R^2$ is methyl, $R^3$ is bromine, $R^4$ is hydrogen, $R^5_y$ is hydrogen and $R^1$ for each compound corresponds to a group of Table A.

Table 59

Compounds of the general formula IA.9, where $R^2$ is methyl, $R^3$ is bromine, $R^4$ is hydrogen, $R^5_y$ is hydrogen and $R^1$ for each compound corresponds to a group of Table A.

Table 60

Compounds of the general formula IA.10, where $R^2$ is methyl, $R^3$ is bromine, $R^4$ is hydrogen, $R^5_y$ is hydrogen and $R^1$ for each compound corresponds to a group of Table A.

Table 61

Compounds of the general formula IA.1, where $R^2$ is methyl, $R^3$ is trifluoromethyl, $R^4$ is hydrogen, $R^5_y$ is hydrogen and $R^1$ for each compound corresponds to a group of Table A.

Table 62

Compounds of the general formula IA.2, where $R^2$ is methyl, $R^3$ is trifluoromethyl, $R^4$ is hydrogen, $R^5_y$ is hydrogen and $R^1$ for each compound corresponds to a group of Table A.

Table 63

Compounds of the general formula IA.3, where $R^2$ is methyl, $R^3$ is trifluoromethyl, $R^4$ is hydrogen, $R^5_y$ is hydrogen and $R^1$ for each compound corresponds to a group of Table A.

Table 64

Compounds of the general formula IA.4, where $R^2$ is methyl, $R^3$ is trifluoromethyl, $R^4$ is hydrogen, $R^5_y$ is hydrogen and $R^1$ for each compound corresponds to a group of Table A.

Table 65

Compounds of the general formula IA.5, where $R^2$ is methyl, $R^3$ is trifluoromethyl, $R^4$ is hydrogen, $R^5_y$ is hydrogen and $R^1$ for each compound corresponds to a group of Table A.

Table 66

Compounds of the general formula IA.6, where $R^2$ is methyl, $R^3$ is trifluoromethyl, $R^4$ is hydrogen, $R^5_y$ is hydrogen and $R^1$ for each compound corresponds to a group of Table A.

Table 67

Compounds of the general formula IA.7, where $R^2$ is methyl, $R^3$ is trifluoromethyl, $R^4$ is hydrogen, $R^5_y$ is hydrogen and $R^1$ for each compound corresponds to a group of Table A.

Table 68

Compounds of the general formula IA.8, where $R^2$ is methyl, $R^3$ is trifluoromethyl, $R^4$ is hydrogen, $R^5_y$ is hydrogen and $R^1$ for each compound corresponds to a group of Table A.

Table 69

Compounds of the general formula IA.9, where $R^2$ is methyl, $R^3$ is trifluoromethyl, $R^4$ is hydrogen, $R^5_y$ is hydrogen and $R^1$ for each compound corresponds to a group of Table A.

Table 70

Compounds of the general formula IA.10, where $R^2$ is methyl, $R^3$ is trifluoromethyl, $R^4$ is hydrogen, $R^5_y$ is hydrogen and $R^1$ for each compound corresponds to a group of Table A.

TABLE A

| No. | $R^1$ |
|---|---|
| A.1 | H |
| A.2 | $CH_3$ |
| A.3 | $C_2H_5$ |
| A.4 | $n-C_3H_7$ |
| A.5 | $i-C_3H_7$ |
| A.6 | cyclopropyl |
| A.7 | $n-C_4H_9$ |
| A.8 | $s-C_4H_9$ |
| A.9 | $i-C_4H_9$ |
| A.10 | $t-C_4H_9$ |
| A.11 | $n-C_5H_{11}$ |
| A.12 | $i-C_5H_{11}$ |
| A.13 | $neo-C_5H_{11}$ |
| A.14 | cyclopentyl |
| A.15 | $n-C_6H_{13}$ |
| A.16 | cyclohexyl |
| A.17 | $n-C_8H_{17}$ |
| A.18 | $CH_2CH_2Cl$ |
| A.19 | $(CH_2)_4Cl$ |
| A.20 | $CH_2CN$ |
| A.21 | $CH_2CH_2CN$ |
| A.22 | $(CH_2)_3CN$ |
| A.23 | $(CH_2)_4CN$ |
| A.24 | $(CH_2)_6CN$ |
| A.25 | cyclohexylmethyl |
| A.26 | 2-cyclohexyleth-1-yl |
| A.27 | cyclopropylmethyl |
| A.28 | 2-cyclopropyleth-1-yl |
| A.29 | 2-methoxyeth-1-yl |
| A.30 | 2-ethoxyeth-1-yl |
| A.31 | 2-isopropoxyeth-1-yl |
| A.32 | 3-methoxyprop-1-yl |
| A.33 | 3-ethoxyprop-1-yl |
| A.34 | 3-isopropoxyprop-1-yl |
| A.35 | 4-methoxybut-1-yl |
| A.36 | 4-isopropoxybut-1-yl |
| A.37 | propen-3-yl |
| A.38 | but-2-en-1-yl |
| A.39 | 3-methylbut-2-en-1-yl |
| A.40 | 2-vinyloxyeth-1-yl |
| A.41 | allyloxyeth-1-yl |
| A.42 | 2-trifluoromethoxyeth-1-yl |
| A.43 | 3-trifluoromethoxyprop-1-yl |
| A.44 | 4-difluoromethoxybut-1-yl |
| A.45 | hydroxycarbonylmethyl |
| A.46 | methoxycarbonylmethyl |
| A.47 | aminocarbonylmethyl |
| A.48 | N-methylaminocarbonylmethyl |
| A.49 | N,N-dimethylaminocarbonyl-methyl |
| A.50 | 2-hydroxycarbonyleth-1-yl |
| A.51 | 2-methoxycarbonyleth-1-yl |
| A.52 | 2-aminocarbonyleth-1-yl |
| A.53 | 2-N-methylaminocarbonyleth-1-yl |
| A.54 | 2-dimethylaminocarbonyleth-1-yl |
| A.55 | 2-aminoeth-1-yl |
| A.56 | 2-aminoprop-1-yl |
| A.57 | 4-aminobut-1-yl |
| A.58 | 3-dimethylaminoprop-1-yl |
| A.59 | 4-aminothiocarbonylbut-1-yl |
| A.60 | 2-oxopropyl |
| A.61 | cyclohexyl |

TABLE A-continued

| No. | R¹ |
|---|---|
| A.62 | cyclopropyl |
| A.63 | cyclopentyl |
| A.64 | 2-methoxyiminoprop-1-yl |
| A.65 | 2-methoxyiminoeth-1-yl |
| A.66 | 6-aminocarbonylhex-1-yl |
| A.67 | 3-aminothiocarbonylprop-1-yl |
| A.68 | 2-aminothiocarbonyleth-1-yl |
| A.69 | aminothiocarbonylmethyl |
| A.70 | 4-(N,N-dimethylamino)but-1-yl |
| A.71 | 2-(methylthio)eth-1-yl |
| A.72 | 2-(methylsulfonyl)eth-1-yl |
| A.73 | 4-(methylthio)prop-1-yl |
| A.74 | 4-(methylsulfonyl)prop-1-yl |
| A.75 | benzyl |
| A.76 | 2-F—C$_6$H$_4$—CH$_2$ |
| A.77 | 3-F—C$_6$H$_4$—CH$_2$ |
| A.78 | 4-F—C$_6$H$_4$—CH$_2$ |
| A.79 | 2,3-F$_2$—C$_6$H$_3$—CH$_2$ |
| A.80 | 2,4-F$_2$—C$_6$H$_3$—CH$_2$ |
| A.81 | 2,5-F$_2$—C$_6$H$_3$—CH$_2$ |
| A.82 | 2,6-F$_2$—C$_6$H$_3$—CH$_2$ |
| A.83 | 3,4-F$_2$—C$_6$H$_3$—CH$_2$ |
| A.84 | 3,5-F$_2$—C$_6$H$_3$—CH$_2$ |
| A.85 | 2-Cl—C$_6$H$_4$—CH$_2$ |
| A.86 | 3-Cl—C$_6$H$_4$—CH$_2$ |
| A.87 | 4-Cl—C$_6$H$_4$—CH$_2$ |
| A.88 | 2,3-Cl$_2$—C$_6$H$_3$—CH$_2$ |
| A.89 | 2,4-Cl$_2$—C$_6$H$_3$—CH$_2$ |
| A.90 | 2,5-Cl$_2$—C$_6$H$_3$—CH$_2$ |
| A.91 | 2,6-Cl$_2$—C$_6$H$_3$—CH$_2$ |
| A.92 | 3,4-Cl$_2$—C$_6$H$_3$—CH$_2$ |
| A.93 | 3,5-Cl$_2$—C$_6$H$_3$—CH$_2$ |
| A.94 | 2,3,4-Cl$_3$—C$_6$H$_2$—CH$_2$ |
| A.95 | 2,3,5-Cl$_3$—C$_6$H$_2$—CH$_2$ |
| A.96 | 2,3,6-Cl$_3$—C$_6$H$_2$—CH$_2$ |
| A.97 | 2,4,5-Cl$_3$—C$_6$H$_2$—CH$_2$ |
| A.98 | 2,4,6-Cl$_3$—C$_6$H$_2$—CH$_2$ |
| A.99 | 3,4,5-Cl$_3$—C$_6$H$_2$—CH$_2$ |
| A.100 | 2-Br—C$_6$H$_4$—CH$_2$ |
| A.101 | 3-Br—C$_6$H$_4$—CH$_2$ |
| A.102 | 4-Br—C$_6$H$_4$—CH$_2$ |
| A.103 | 2,3-Br$_2$—C$_6$H$_3$—CH$_2$ |
| A.104 | 2,4-Br$_2$—C$_6$H$_3$—CH$_2$ |
| A.105 | 2,5-Br$_2$—C$_6$H$_3$—CH$_2$ |
| A.106 | 2,6-Br$_2$—C$_6$H$_3$—CH$_2$ |
| A.107 | 3,4-Br$_2$—C$_6$H$_3$—CH$_2$ |
| A.108 | 3,5-Br$_2$—C$_6$H$_3$—CH$_2$ |
| A.109 | 2-F, 3-Cl—C$_6$H$_3$—CH$_2$ |
| A.110 | 2-F, 4-Cl—C$_6$H$_3$—CH$_2$ |
| A.111 | 2-F, 5-Cl—C$_6$H$_3$—CH$_2$ |
| A.112 | 2-F, 3-Br—C$_6$H$_3$—CH$_2$ |
| A.113 | 2-F, 4-Br—C$_6$H$_3$—CH$_2$ |
| A.114 | 2-F, 5-Br—C$_6$H$_3$—CH$_2$ |
| A.115 | 2-Cl, 3-Br—C$_6$H$_3$—CH$_2$ |
| A.116 | 2-Cl, 4-Br—C$_6$H$_3$—CH$_2$ |
| A.117 | 2-Cl, 5-Br—C$_6$H$_3$—CH$_2$ |
| A.118 | 3-F, 4-Cl—C$_6$H$_3$—CH$_2$ |
| A.119 | 3-F, 5-Cl—C$_6$H$_3$—CH$_2$ |
| A.120 | 3-F, 6-Cl—C$_6$H$_3$—CH$_2$ |
| A.121 | 3-F, 4-Br—C$_6$H$_3$—CH$_2$ |
| A.122 | 3-F, 5-Br—C$_6$H$_3$—CH$_2$ |
| A.123 | 3-F, 6-Br—C$_6$H$_3$—CH$_2$ |
| A.124 | 3-Cl, 4-Br—C$_6$H$_3$—CH$_2$ |
| A.125 | 3-Cl, 5-Br—C$_6$H$_3$—CH$_2$ |
| A.126 | 3-Cl, 6-Br—C$_6$H$_3$—CH$_2$ |
| A.127 | 4-F, 5-Cl—C$_6$H$_3$—CH$_2$ |
| A.128 | 4-F, 6-Cl—C$_6$H$_3$—CH$_2$ |
| A.129 | 4-F, 5-Br—C$_6$H$_3$—CH$_2$ |
| A.130 | 4-F, 6-Br—C$_6$H$_3$—CH$_2$ |
| A.131 | 4-Cl, 5-Br—C$_6$H$_3$—CH$_2$ |
| A.132 | 5-F, 6-Cl—C$_6$H$_3$—CH$_2$ |
| A.133 | 5-F, 6-Br—C$_6$H$_3$—CH$_2$ |
| A.134 | 5-Cl, 6-Br—C$_6$H$_3$—CH$_2$ |
| A.135 | 3-Br, 4-Cl, 5-Br—C$_6$H$_2$—CH$_2$ |
| A.136 | 2-CN—C$_6$H$_4$—CH$_2$ |
| A.137 | 3-CN—C$_6$H$_4$—CH$_2$ |
| A.138 | 4-CN—C$_6$H$_4$—CH$_2$ |
| A.139 | 2-NO$_2$—C$_6$H$_4$—CH$_2$ |
| A.140 | 3-NO$_2$—C$_6$H$_4$—CH$_2$ |
| A.141 | 4-NO$_2$—C$_6$H$_4$—CH$_2$ |
| A.142 | 2-CH$_3$—C$_6$H$_4$—CH$_2$ |
| A.143 | 3-CH$_3$—C$_6$H$_4$—CH$_2$ |
| A.144 | 4-CH$_3$—C$_6$H$_4$—CH$_2$ |
| A.145 | 2,3-(CH$_3$)$_2$—C$_6$H$_3$—CH$_2$ |
| A.146 | 2,4-(CH$_3$)$_2$—C$_6$H$_3$—CH$_2$ |
| A.147 | 2,5-(CH$_3$)$_2$—C$_6$H$_3$—CH$_2$ |
| A.148 | 2,6-(CH$_3$)$_2$—C$_6$H$_3$—CH$_2$ |
| A.149 | 3,4-(CH$_3$)$_2$—C$_6$H$_3$—CH$_2$ |
| A.150 | 3,5-(CH$_3$)$_2$—C$_6$H$_3$—CH$_2$ |
| A.151 | 2-C$_2$H$_5$—C$_6$H$_4$—CH$_2$ |
| A.152 | 3-C$_2$H$_5$—C$_6$H$_4$—CH$_2$ |
| A.153 | 4-C$_2$H$_5$—C$_6$H$_4$—CH$_2$ |
| A.154 | 2-i-C$_3$H$_7$—C$_6$H$_4$—CH$_2$ |
| A.155 | 3-i-C$_3$H$_7$—C$_6$H$_4$—CH$_2$ |
| A.156 | 4-i-C$_3$H$_7$—C$_6$H$_4$—CH$_2$ |
| A.157 | 2-cyclohexyl-C$_6$H$_4$—CH$_2$ |
| A.158 | 3-cyclohexyl-C$_6$H$_4$—CH$_2$ |
| A.159 | 4-cyclohexyl-C$_6$H$_4$—CH$_2$ |
| A.160 | 2-vinyl-C$_6$H$_4$—CH$_2$ |
| A.161 | 3-vinyl-C$_6$H$_4$—CH$_2$ |
| A.162 | 4-vinyl-C$_6$H$_4$—CH$_2$ |
| A.163 | 2-allyl-C$_6$H$_4$—CH$_2$ |
| A.164 | 3-allyl-C$_6$H$_4$—CH$_2$ |
| A.165 | 4-allyl-C$_6$H$_4$—CH$_2$ |
| A.166 | 2-C$_6$H$_5$—C$_6$H$_4$—CH$_2$ |
| A.167 | 3-C$_6$H$_5$—C$_6$H$_4$—CH$_2$ |
| A.168 | 4-C$_6$H$_5$—C$_6$H$_4$—CH$_2$ |
| A.169 | 3-CH$_3$, 5-t-C$_4$H$_9$—C$_6$H$_3$—CH$_2$ |
| A.170 | 2-OH—C$_6$H$_4$—CH$_2$ |
| A.171 | 3-OH—C$_6$H$_4$—CH$_2$ |
| A.172 | 4-OH—C$_6$H$_4$—CH$_2$ |
| A.173 | 2-OCH$_3$—C$_6$H$_4$—CH$_2$ |
| A.174 | 3-OCH$_3$—C$_6$H$_4$—CH$_2$ |
| A.175 | 4-OCH$_3$—C$_6$H$_4$—CH$_2$ |
| A.176 | 2,3-(OCH$_3$)$_2$—C$_6$H$_3$—CH$_2$ |
| A.177 | 2,4-(OCH$_3$)$_2$—C$_6$H$_3$—CH$_2$ |
| A.178 | 2,5-(OCH$_3$)$_2$—C$_6$H$_3$—CH$_2$ |
| A.179 | 3,4-(OCH$_3$)$_2$—C$_6$H$_3$—CH$_2$ |
| A.180 | 3,5-(OCH$_3$)$_2$—C$_6$H$_3$—CH$_2$ |
| A.181 | 3,4,5-(OCH$_3$)$_3$—C$_6$H$_2$—CH$_2$ |
| A.182 | 2-OC$_2$H$_5$—C$_6$H$_4$—CH$_2$ |
| A.183 | 3-OC$_2$H$_5$—C$_6$H$_4$—CH$_2$ |
| A.184 | 4-OC$_2$H$_5$—C$_6$H$_4$—CH$_2$ |
| A.185 | 2-O-(n-C$_3$H$_7$)—C$_6$H$_4$—CH$_2$ |
| A.186 | 3-O-(n-C$_3$H$_7$)—C$_6$H$_4$—CH$_2$ |
| A.187 | 4-O-(n-C$_3$H$_7$)—C$_6$H$_4$—CH$_2$ |
| A.188 | 2-O-(i-C$_3$H$_7$)—C$_6$H$_4$—CH$_2$ |
| A.189 | 3-O-(i-C$_3$H$_7$)—C$_6$H$_4$—CH$_2$ |
| A.190 | 4-O-(i-C$_3$H$_7$)—C$_6$H$_4$—CH$_2$ |
| A.191 | 4-O-(n-C$_4$H$_9$)—C$_6$H$_4$—CH$_2$ |
| A.192 | 3-O-(t-C$_4$H$_9$)—C$_6$H$_4$—CH$_2$ |
| A.193 | 4-O-(n-C$_6$H$_{13}$)—C$_6$H$_4$—CH$_2$ |
| A.194 | 2-O-allyl-C$_6$H$_4$—CH$_2$ |
| A.195 | 3-O-allyl-C$_6$H$_4$—CH$_2$ |
| A.196 | 4-O-allyl-C$_6$H$_4$—CH$_2$ |
| A.197 | 2-CF$_3$—C$_6$H$_4$—CH$_2$ |
| A.198 | 3-CF$_3$—C$_6$H$_4$—CH$_2$ |
| A.199 | 4-CF$_3$—C$_6$H$_4$—CH$_2$ |
| A.200 | 2-acetyl-C$_6$H$_4$—CH$_2$ |
| A.201 | 3-acetyl-C$_6$H$_4$—CH$_2$ |
| A.202 | 4-acetyl-C$_6$H$_4$—CH$_2$ |
| A.203 | 2-methoxycarbonyl-C$_6$H$_4$—CH$_2$ |
| A.204 | 3-methoxycarbonyl-C$_6$H$_4$—CH$_2$ |
| A.205 | 4-methoxycarbonyl-C$_6$H$_4$—CH$_2$ |
| A.206 | 2-aminocarbonyl-C$_6$H$_4$—CH$_2$ |
| A.207 | 3-aminocarbonyl-C$_6$H$_4$—CH$_2$ |
| A.208 | 4-aminocarbonyl-C$_6$H$_4$—CH$_2$ |
| A.209 | 2-dimethylaminocarbonyl-C$_6$H$_4$—CH$_2$ |
| A.210 | 3-dimethylaminocarbonyl-C$_6$H$_4$—CH$_2$ |
| A.211 | 4-dimethylaminocarbonyl-C$_6$H$_4$—CH$_2$ |
| A.212 | 2-(N-methylaminocarbonyl)-C$_6$H$_4$—CH$_2$ |
| A.213 | 3-(N-methylaminocarbonyl)-C$_6$H$_4$—CH$_2$ |
| A.214 | 4-(N-methylaminocarbonyl)-C$_6$H$_4$—CH$_2$ |
| A.215 | 2-H$_2$N—C$_6$H$_4$—CH$_2$ |

TABLE A-continued

| No. | R¹ |
|---|---|
| A.216 | 3-H₂N—C₆H₄—CH₂ |
| A.217 | 4-H₂N—C₆H₄—CH₂ |
| A.218 | 2-aminothiocarbonyl-C₆H₄—CH₂ |
| A.219 | 3-aminothiocarbonyl-C₆H₄—CH₂ |
| A.220 | 4-aminothiocarbonyl-C₆H₄—CH₂ |
| A.221 | 2-methoxyiminomethyl-C₆H₄—CH₂ |
| A.222 | 3-methoxyiminomethyl-C₆H₄—CH₂ |
| A.223 | 4-methoxyiminomethyl-C₆H₄—CH₂ |
| A.224 | 2-formyl-C₆H₄—CH₂ |
| A.225 | 3-formyl-C₆H₄—CH₂ |
| A.226 | 4-formyl-C₆H₄—CH₂ |
| A.227 | 2-(1'-methoxyiminoeth-1'-yl)-C₆H₄—CH₂ |
| A.228 | 3-(1'-methoxyiminoeth-1'-yl)-C₆H₄—CH₂ |
| A.229 | 4-(1'-methoxyiminoeth-1'-yl)-C₆H₄—CH₂ |
| A.230 | 2-SCH₃—C₆H₄—CH₂ |
| A.231 | 3-SCH₃—C₆H₄—CH₂ |
| A.232 | 4-SCH₃—C₆H₄—CH₂ |
| A.233 | 2-SO₂CH₃—C₆H₄—CH₂ |
| A.234 | 3-SO₂CH₃—C₆H₄—CH₂ |
| A.235 | 4-SO₂CH₃—C₆H₄—CH₂ |
| A.236 | 2-OCF₃—C₆H₄—CH₂ |
| A.237 | 3-OCF₃—C₆H₄—CH₂ |
| A.238 | 4-OCF₃—C₆H₄—CH₂ |
| A.239 | 2-OCHF₂—C₆H₄—CH₂ |
| A.240 | 3-OCHF₂—C₆H₄—CH₂ |
| A.241 | 4-OCHF₂—C₆H₄—CH₂ |
| A.242 | 3-CF₃, 4-OCF₃—C₆H₃—CH₂ |
| A.243 | 1-naphthyl-CH₂ |
| A.244 | 2-naphthyl-CH₂ |
| A.245 | 2-phenoxyeth-1-yl |
| A.246 | 2-(2'-chlorophenoxy)eth-1-yl |
| A.247 | 2-(3'-chlorophenoxy)eth-1-yl |
| A.248 | 2-(4'-chlorophenoxy)eth-1-yl |
| A.249 | 2-(3',5'-dichlorophenoxy)eth-1-yl |
| A.250 | 2-(2'-cyanophenoxy)eth-1-yl |
| A.251 | 2-(3'-cyanophenoxy)eth-1-yl |
| A.252 | 2-(4'-cyanophenoxy)eth-1-yl |
| A.253 | 2-(2'-methylphenoxy)eth-1-yl |
| A.254 | 2-(3'-methylphenoxy)eth-1-yl |
| A.255 | 2-(4'-methylphenoxy)eth-1-yl |
| A.256 | 2-(3'-t-butylphenoxy)eth-1-yl |
| A.257 | 2-(4'-t-butylphenoxy)eth-1-yl |
| A.258 | 2-(2'-nitrophenoxy)eth-1-yl |
| A.259 | 2-(3'-nitrophenoxy)eth-1-yl |
| A.260 | 2-(4'-nitrophenoxy)eth-1-yl |
| A.261 | 2-(2'-methoxyphenoxy)eth-1-yl |
| A.262 | 2-(3'-methoxyphenoxy)eth-1-yl |
| A.263 | 2-(4'-methoxyphenoxy)eth-1-yl |
| A.264 | 2-(2'-trifluoromethylphenoxy)eth-1-yl |
| A.265 | 2-(3'-trifluoromethylphenoxy)eth-1-yl |
| A.266 | 2-(4'-trifluoromethylphenoxy)eth-1-yl |
| A.267 | 2-(2'-acetylphenoxy)eth-1-yl |
| A.268 | 2-(3'-acetylphenoxy)eth-1-yl |
| A.269 | 2-(4'-acetylphenoxy)eth-1-yl |
| A.270 | 2-(2'-methoxycarbonyl)eth-1-yl |
| A.271 | 2-(3'-methoxycarbonyl)eth-1-yl |
| A.272 | 2-(4'-methoxycarbonyl)eth-1-yl |
| A.273 | 2-(2'-dimethylaminocarbonyl)eth-1-yl |
| A.274 | 2-(3'-dimethylaminocarbonyl)eth-1-yl |
| A.275 | 2-(4'-dimethylaminocarbonyl)eth-1-yl |
| A.276 | 2-(2'-aminothiocarbonyl)eth-1-yl |
| A.277 | 2-(3'-aminothiocarbonyl)eth-1-yl |
| A.278 | 2-(4'-aminothiocarbonyl)eth-1-yl |
| A.279 | 2-(2'-methylsulfonyl)eth-1-yl |
| A.280 | 2-(3'-methylsulfonyl)eth-1-yl |
| A.281 | 2-(4'-methylsulfonyl)eth-1-yl |
| A.282 | 3-phenoxyprop-1-yl |
| A.283 | 3-(2'-chlorophenoxy)prop-1-yl |
| A.284 | 3-(3'-chlorophenoxy)prop-1-yl |
| A.285 | 3-(4'-chlorophenoxy)prop-1-yl |
| A.286 | 3-(3',5',dichlorophenoxy)prop-1-yl |
| A.287 | 3-(2'-cyanophenoxy)prop-1-yl |
| A.288 | 3-(3'-cyanophenoxy)prop-1-yl |
| A.289 | 3-(4'-cyanophenoxy)prop-1-yl |
| A.290 | 3-(2'-methylphenoxy)prop-1-yl |
| A.291 | 3-(3'-methylphenoxy)prop-1-yl |
| A.292 | 3-(4'-methylphenoxy)prop-1-yl |
| A.293 | 3-(2'-methoxyphenoxy)prop-1-yl |
| A.294 | 3-(3'-methoxyphenoxy)prop-1-yl |
| A.295 | 3-(4'-methoxyphenoxy)prop-1-yl |
| A.296 | 3-(2'-trifluoromethylphenoxy)prop-1-yl |
| A.297 | 3-(3'-trifluoromethylphenoxy)prop-1-yl |
| A.298 | 3-(4'-trifluoromethylphenoxy)prop-1-yl |
| A.299 | 4-phenoxybut-1-yl |
| A.300 | 2-phenyleth-1-yl |
| A.301 | 2-(2'-chlorophenyl)eth-1-yl |
| A.302 | 2-(3'-chlorophenyl)eth-1-yl |
| A.303 | 2-(4'-chlorophenyl)eth-1-yl |
| A.304 | 2-(3',5'-dichlorophenyl)eth-1-yl |
| A.305 | 2-(2'-cyanophenyl)eth-1-yl |
| A.306 | 2-(3'-cyanophenyl)eth-1-yl |
| A.307 | 2-(4'-cyanophenyl)eth-1-yl |
| A.308 | 2-(2'-methylphenyl)eth-1-yl |
| A.309 | 2-(3'-methylphenyl)eth-1-yl |
| A.310 | 2-(4'-methylphenyl)eth-1-yl |
| A.311 | 2-(2'-methoxyphenyl)eth-1-yl |
| A.312 | 2-(3'-methoxyphenyl)eth-1-yl |
| A.313 | 2-(4'-methoxyphenyl)eth-1-yl |
| A.314 | 2-(2'-trifluoromethylphenyl)eth-1-yl |
| A.315 | 2-(3'-trifluoromethylphenyl)eth-1-yl |
| A.316 | 2-(4'-trifluoromethylphenyl)eth-1-yl |
| A.317 | 3-phenylprop-1-yl |
| A.318 | 3-(2'-chlorophenyl) prop-1-yl |
| A.319 | 3-(3'-chlorophenyl)prop-1-yl |
| A.320 | 3-(4'-chlorophenyl)prop-1-yl |
| A.321 | 3-(2'-cyanophenyl)prop-1-yl |
| A.322 | 3-(3'-cyanophenyl)prop-1-yl |
| A.323 | 3-(4'-cyanophenyl)prop-1-yl |
| A.324 | 3-(2'-trifluoromethylphenyl)prop-1-yl |
| A.325 | 4-phenylbut-1-yl |
| A.326 | 4-(4'-chlorophenyl)but-1-yl |
| A.327 | 6-(4'-chlorophenyl)hex-1-yl |
| A.328 | 2-pyridylmethyl |
| A.329 | 3-pyridylmethyl |
| A.330 | 4-pyridylmethyl |
| A.331 | 4-chloropyridin-2-ylmethyl |
| A.332 | 5-chloropyridin-2-ylmethyl |
| A.333 | 6-chloropyridin-2-ylmethyl |
| A.334 | 5-chloropyridin-3-ylmethyl |
| A.335 | 6-chloropyridin-3-ylmethyl |
| A.336 | 2-chloropyridin-4-ylmethyl |
| A.337 | 2-pyrimidinylmethyl |
| A.338 | 4-chloropyrimidin-2-ylmethyl |
| A.339 | 5-chloropyrimidin-2-ylmethyl |
| A.340 | 2-chloropyrimidin-4-ylmethyl |
| A.341 | 6-chloropyrimidin-4-ylmethyl |
| A.342 | 2-chloropyrimidin-5-ylmethyl |
| A.343 | 4-pyridazinylmethyl |
| A.344 | 2-pyrazinylmethyl |
| A.345 | 5-chloropyrazin-2-ylmethyl |
| A.346 | 6-chloropyrazin-2-ylmethyl |
| A.347 | 3-pyridazinylmethyl |
| A.348 | 6-chloropyridazin-3-ylmethyl |
| A.349 | 1,3,5-triazinylmethyl |
| A.350 | 2-furylmethyl |
| A.351 | 3-furylmethyl |
| A.352 | 4-bromofur-2-ylmethyl |
| A.353 | 5-chlorofur-2-ylmethyl |
| A.354 | 2-thienylmethyl |
| A.355 | 3-thienylmethyl |
| A.356 | 5-methylthien-3-ylmethyl |
| A.357 | 5-chlorothien-2-ylmethyl |
| A.358 | 2-chlorothien-4-ylmethyl |
| A.359 | 2-pyrrolylmethyl |
| A.360 | 3-pyrrolylmethyl |
| A.361 | 2-oxazolylmethyl |
| A.362 | 4-methyloxazol-2-ylmethyl |
| A.363 | 5-methyloxazol-2-ylmethyl |
| A.364 | 4-chlorooxazol-2-ylmethyl |
| A.365 | 5-chlorooxazol-2-ylmethyl |
| A.366 | 4-oxazolylmethyl |
| A.367 | 2-methyloxazol-4-ylmethyl |
| A.368 | 5-methyloxazol-4-ylmethyl |
| A.369 | 2-chlorooxazol-4-ylmethyl |

TABLE A-continued

| No. | R¹ |
|---|---|
| A.370 | 5-chlorooxazol-4-ylmethyl |
| A.371 | 5-oxazolylmethyl |
| A.372 | 2-methyloxazol-5-ylmethyl |
| A.373 | 4-methyloxazol-5-ylmethyl |
| A.374 | 2-chlorooxazol-5-ylmethyl |
| A.375 | 4-chlorooxazol-5-ylmethyl |
| A.376 | 2-thiazolylmethyl |
| A.377 | 4-methylthiazol-2-ylmethyl |
| A.378 | 5-methylthiazol-2-ylmethyl |
| A.379 | 4-chlorothiazol-2-ylmethyl |
| A.380 | 5-chlorothiazol-2-ylmethyl |
| A.381 | 4-thiazolylmethyl |
| A.382 | 2-methylthiazol-4-ylmethyl |
| A.383 | 5-methylthiazol-4-ylmethyl |
| A.384 | 2-chlorothiazol-4-ylmethyl |
| A.385 | 5-chlorothiazol-4-ylmethyl |
| A.386 | 5-thiazolylmethyl |
| A.387 | 2-methylthiazol-5-ylmethyl |
| A.388 | 4-methylthiazol-5-ylmethyl |
| A.389 | 2-chlorothiazol-5-ylmethyl |
| A.390 | 4-chlorothiazol-5-ylmethyl |
| A.391 | 3-isoxazolylmethyl |
| A.392 | 4-methylisoxazol-3-ylmethyl |
| A.393 | 5-methylisoxazol-3-ylmethyl |
| A.394 | 4-chloroisoxazol-3-ylmethyl |
| A.395 | 5-chloroisoxazol-3-ylmethyl |
| A.396 | 4-isoxazolylmethyl |
| A.397 | 3-methylisoxazol-4-ylmethyl |
| A.398 | 5-methylisoxazol-4-ylmethyl |
| A.399 | 3-chloroisoxazol-4-ylmethyl |
| A.400 | 5-chloroisoxazol-4-ylmethyl |
| A.401 | 5-isoxazolylmethyl |
| A.402 | 3-methylisoxazol-5-ylmethyl |
| A.403 | 4-methylisoxazol-5-ylmethyl |
| A.404 | 3-chloroisoxazol-5-ylmethyl |
| A.405 | 4-chloroisoxazol-5-ylmethyl |
| A.406 | 3-isothiazolylmethyl |
| A.407 | 4-methylisothiazol-3-ylmethyl |
| A.408 | 5-methylisothiazol-3-ylmethyl |
| A.409 | 4-chloroisothiazol-3-ylmethyl |
| A.410 | 5-chloroisothiazol-3-ylmethyl |
| A.411 | 4-isothiazolylmethyl |
| A.412 | 3-methylisothiazol-4-ylmethyl |
| A.413 | 5-methylisothiazol-4-ylmethyl |
| A.414 | 3-chloroisothiazol-4-ylmethyl |
| A.415 | 5-chloroisothiazol-4-ylmethyl |
| A.416 | 5-isothiazolylmethyl |
| A.417 | 3-methylisothiazol-5-ylmethyl |
| A.418 | 4-methylisothiazol-5-ylmethyl |
| A.419 | 3-chloroisothiazol-5-ylmethyl |
| A.420 | 4-chloroisothiazol-5-ylmethyl |
| A.421 | 4-imidazolylmethyl |
| A.422 | 1-phenylpyrazol-3-ylmethyl |
| A.423 | 1-methylimidazol-4-ylmethyl |
| A.424 | 1-phenyl-1,2,4-triazol-3-ylmethyl |
| A.425 | 1,2,4-oxadiazol-3-ylmethyl |
| A.426 | 5-chloro-1,2,4-oxadiazol-3-ylmethyl |
| A.427 | 5-methyl-1,2,4-oxadiazol-3-ylmethyl |
| A.428 | 5-trifluoromethyl-1,2,4-oxadiazol-3-ylmethyl |
| A.429 | 1,3,4-oxadiazol-2-ylmethyl |
| A.430 | 5-chloro-1,3,4-oxadiazol-2-ylmethyl |
| A.431 | 5-methyl-1,3,4-oxadiazol-2-ylmethyl |
| A.432 | 5-methoxy-1,3,4-oxadiazol-2-ylmethyl |
| A.433 | 1,2,4-thiadiazol-3-ylmethyl |
| A.434 | 5-chloro-1,2,4-thiadiazol-3-ylmethyl |
| A.435 | 5-methyl-1,2,4-thiadiazol-3-ylmethyl |
| A.436 | 1,3,4-thiadiazol-2-ylmethyl |
| A.437 | 5-chloro-1,3,4-thiadiazol-2-ylmethyl |
| A.438 | 5-methyl-1,3,4-thiadiazol-2-ylmethyl |
| A.439 | 5-cyano-1,3,4-thiadiazol-2-ylmethyl |
| A.440 | 2-(2'-pyridinyloxy)eth-1-yl |
| A.441 | 2-(3'-pyridinyloxy)eth-1-yl |
| A.442 | 2-(4'-pyridinyloxy)eth-1-yl |
| A.443 | 2-(2'-pyrimidinyloxy)eth-1-yl |
| A.444 | 2-(4'-pyrimidinyloxy)eth-1-yl |
| A.445 | 2-(5'-pyrimidinyloxy)eth-1-yl |
| A.446 | 2-(2'-pyrazinyloxy)eth-1-yl |
| A.447 | 2-(2'-pyridazinyloxy)eth-1-yl |
| A.448 | 2-(3'-pyridazinyloxy)eth-1-yl |
| A.449 | 2-(1',3',5'-triazinyloxy)eth-1-yl |
| A.450 | 2-(5'-methylisoxazol-3'-yloxy)eth-1-yl |
| A.451 | 2-(5'-chloroisoxazol-3'-yloxy)eth-1-yl |
| A.452 | 2-(2'-methoxythiazol-4'-yloxy)eth-1-yl |
| A.453 | 2-(4'-chlorooxazol-2'-yloxy)eth-1-yl |
| A.454 | 2-(1'-phenyl-1'H-1',2',4'-triazol-3'-yloxy)eth-1-yl |
| A.455 | 2-(1'-phenylpyrazol-3'-yloxy)eth-1-yl |
| A.456 | $C_6H_5$ |
| A.457 | 2-Cl—$C_6H_4$ |
| A.458 | 3-Cl—$C_6H_4$ |
| A.459 | 4-Cl—$C_6H_4$ |
| A.460 | 2,3-$Cl_2$—$C_6H_3$ |
| A.461 | 2,4-$Cl_2$—$C_6H_3$ |
| A.462 | 2,5-$Cl_2$—$C_6H_3$ |
| A.463 | 3,4-$Cl_2$—$C_6H_3$ |
| A.464 | 3,5-$Cl_2$—$C_6H_3$ |
| A.465 | 4-CN—$C_6H_4$ |
| A.466 | 2-$NO_2$—$C_6H_4$ |
| A.467 | 3-$NO_2$—$C_6H_4$ |
| A.468 | 4-$NO_2$—$C_6H_4$ |
| A.469 | 2,4-$(NO_2)_2$—$C_6H_3$ |
| A.470 | 2-$CH_3$—$C_6H_4$ |
| A.471 | 3-$CH_3$—$C_6H_4$ |
| A.472 | 4-$CH_3$—$C_6H_4$ |
| A.473 | 2,3-$(CH_3)_2$—$C_6H_3$ |
| A.474 | 2,4-$(CH_3)_2$—$C_6H_3$ |
| A.475 | 2,5-$(CH_3)_2$—$C_6H_3$ |
| A.476 | 2,6-$(CH_3)_2$—$C_6H_3$ |
| A.477 | 2-$C_6H_5$—$C_6H_4$ |
| A.478 | 3-$C_6H_5$—$C_6H_4$ |
| A.479 | 4-$C_6H_5$—$C_6H_4$ |
| A.480 | 3-$OCH_3$—$C_6H_4$ |
| A.481 | 4-$OCH_3$—$C_6H_4$ |
| A.482 | 3-acetyl-$C_6H_4$ |
| A.483 | 4-acetyl-$C_6H_4$ |
| A.484 | 3-methoxycarbonyl-$C_6H_4$ |
| A.485 | 4-methoxycarbonyl-$C_6H_4$ |
| A.486 | 3-$CF_3$—$C_6H_4$ |
| A.487 | 4-$CF_3$—$C_6H_4$ |
| A.488 | 2-naphthyl |
| A.489 | 6-chloropyridazin-3-yl |
| A.490 | 5-chloropyrazin-2-yl |
| A.491 | quinolin-2-yl |
| A.492 | 2,5-dimethylpyrazin-3-yl |
| A.493 | pyrazin-2-yl |
| A.494 | 3-chloropyrid-2-yl |
| A.495 | 6-chloropyrid-2-yl |
| A.496 | 4-trifluoromethyl, 6-chloropyrid-2-yl |
| A.497 | 4-trifluoromethylpyrid-2-yl |
| A.498 | 6-trifluoromethylpyrid-2-yl |
| A.499 | 6-methoxypyrid-2-yl |
| A.500 | 5-chloropyrid-2-yl |
| A.501 | pyrid-2-yl |
| A.502 | benzothiazol-2-yl |
| A.503 | 7-chloroquinolin-4-yl |
| A.504 | 3-nitropyrid-2-yl |
| A.505 | pyrrol-3-yl |
| A.506 | pyrrol-2-yl |
| A.507 | 2,6-dioctylpyrid-4-yl |
| A.508 | 5-nitropyrid-2-yl |
| A.509 | pyrid-4-yl |
| A.510 | pyrid-3-yl |
| A.511 | pyrimidin-2-yl |
| A.512 | pyrimidin-4-yl |
| A.513 | quinazolin-4-yl |
| A.514 | 6-chloropyrimidin-4-yl |
| A.515 | 6-methoxypyrimidin-4-yl |
| A.516 | 2,5,6-trichloropyrimidin-4-yl |
| A.517 | 2,6-dimethylpyrimidin-4-yl |
| A.518 | 2-methyl, 6-chloropyrimidin-4-yl |
| A.519 | 2-methyl, 6-ethoxypyrimidin-4-yl |
| A.520 | 4,5,6-trichloropyrimidin-2-yl |
| A.521 | 4,6-dimethoxypyrimidin-2-yl |
| A.522 | 4,6-dimethylpyrimidin-2-yl |
| A.523 | 4,6-dichloropyrimidin-2-yl |

TABLE A-continued

| No. | R¹ |
|---|---|
| A.524 | 4-methyl, 6-methoxypyrimidin-2-yl |
| A.525 | 4-chloro, 6-methoxypyrimidin-2-yl |
| A.526 | 6-chloroquinoxalin-2-yl |
| A.527 | 3,6-dichloro-1,2,4-triazin-5-yl |
| A.528 | 4-methoxy-1,3,5-triazin-2-yl |
| A.529 | 4-ethoxy-1,3,5-triazin-2-yl |
| A.530 | 4-6-dichloro-1,3,5-triazin-2-yl |
| A.531 | 4-ethoxy, 6-chloro-1,3,5-triazin-2-yl |
| A.532 | isoxazol-3-yl |
| A.533 | thien-2-yl |
| A.534 | fur-2-yl |
| A.535 | thiatriazol-5-yl |
| A.536 | (E)-1-chloropropen-3-yl |
| A.537 | (E)-4-(4'-chlorophenyl)but-2-en-1-yl |
| A.538 | propyn-3-yl |
| A.539 | methylcarbonyl |
| A.540 | ethylcarbonyl |
| A.541 | n-propylcarbonyl |
| A.542 | i-propylcarbonyl |
| A.543 | n-butylcarbonyl |
| A.544 | s-butylcarbonyl |
| A.545 | i-butylcarbonyl |
| A.546 | t-butylcarbonyl |
| A.547 | n-pentylcarbonyl |
| A.548 | i-pentylcarbonyl |
| A.549 | neo-pentylcarbonyl |
| A.550 | n-hexylcarbonyl |
| A.551 | n-octylcarbonyl |
| A.552 | 1-propenylcarbonyl |
| A.553 | 2-penten-1-ylcarbonyl |
| A.554 | 2,5-heptadien-1-ylcarbonyl |
| A.555 | benzoyl |
| A.556 | 2-chlorobenzoyl |
| A.557 | 3-chlorobenzoyl |
| A.558 | 4-chlorobenzoyl |
| A.559 | 2-cyanobenzoyl |
| A.560 | 3-cyanobenzoyl |
| A.561 | 4-cyanobenzoyl |
| A.562 | 4-methoxybenzoyl |
| A.563 | 2-pyridylcarbonyl |
| A.564 | 3-pyridylcarbonyl |
| A.565 | 4-pyridylcarbonyl |
| A.566 | 2-pyrimidinylcarbonyl |
| A.567 | 2-oxazolylcarbonyl |
| A.568 | 4-methylisoxazol-5-ylcarbonyl |
| A.569 | methylsulfonyl |
| A.570 | ethylsulfonyl |
| A.571 | n-propylsulfonyl |
| A.572 | i-propylsulfonyl |
| A.573 | n-butylsulfonyl |
| A.574 | t-butylsulfonyl |
| A.575 | n-pentylsulfonyl |
| A.576 | neo-pentylsulfonyl |
| A.577 | n-hexylsulfonyl |
| A.578 | n-octylsulfonyl |
| A.579 | phenylsulfonyl |
| A.580 | 2-chlorophenylsulfonyl |
| A.581 | 3-chlorophenylsulfonyl |
| A.582 | 4-chlorophenylsulfonyl |
| A.583 | 2-cyanophenylsulfonyl |
| A.584 | 3-cyanophenylsulfonyl |
| A.585 | 4-cyanophenylsulfonyl |
| A.586 | 2-pyridylsulfonyl |
| A.587 | 3-pyridylsulfonyl |
| A.588 | 4-pyridylsulfonyl |
| A.589 | 2-pyrimidinylsulfonyl |
| A.590 | 4-oxazolylsulfonyl |
| A.591 | 5-chlorothiazol-2-ylsulfonyl |
| A.592 | 2-t-$C_4H_9$—$C_6H_4$—$CH_2$ |
| A.593 | 3-t-$C_4H_9$—$C_6H_4$—$CH_2$ |
| A.594 | 4-t-$C_4H_9$—$C_6H_4$—$CH_2$ |
| A.595 | 2-(4'-chlorothiazol-2'-yloxy)eth-1-yl |
| A.596 | 2-(1'-methylpyrazol-4'-yloxy)eth-1-yl |
| A.597 | 4-Br—$C_6H_4$ |
| A.598 | 3,5-$(CH_3)_2$—$C_6H_3$ |
| A.599 | 4-$C_2H_5$—$C_6H_4$ |
| A.600 | 3-dimethylaminocarbonyl-$C_6H_4$ |
| A.601 | 4-dimethylaminocarbonyl-$C_6H_4$ |
| A.602 | 2-hydroxyprop-1-yl |
| A.603 | 6-hydroxy-2-methylpyrimidin-4-ylmethyl |
| A.604 | [6-OH, 2-CH($CH_3$)$_2$-pyrimidin-4-yl]—$CH_2$ |
| A.605 | [6-OH, 2-CH($CH_2$)$_2$-pyrimidin-4-yl]—$CH_2$ |
| A.606 | 5-(2'-furan)-pent-1-yl |
| A.607 | 5-(2'-N-methylpyrrole)-pent-1-yl |
| A.608 | [2-(4-Cl—$C_6H_4$)-oxazol-4-yl]—$CH_2$ |
| A.609 | 3-$CF_3$-pyridin-2-yl |
| A.610 | 5-$CF_3$-pyridin-2-yl |
| A.611 | 6-(2'-thienyl)hex-1-yl |

The compounds I are suitable as fungicides.

The compounds I are distinguished by an outstanding activity against a broad spectrum of phytopathogenic fungi, in particular from the classes Ascomycetes, Phycomycetes and Basidiomycetes. Some of them act systemically and can be employed in crop protection as foliar- and soil-acting fungicides.

They are especially important for controlling a large number of fungi on a variety of crop plants such as wheat, rye, barley, oats, rice, corn, grass, cotton, soya beans, coffee, sugar cane, grapevines, fruit species, ornamentals and vegetables such as cucumbers, beans and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, Uncinula necator on grape-vines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, vegetables and ornamentals, grapevines, *Cercospora arachidicola* on peanuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grapevines, Alternaria species on vegetables and fruit.

Moreover, the compounds I are suitable for controlling harmful fungi in the protection of materials eg. wood, paper, fibers or fabrics) and in the protection of stored products.

The compounds I are used by treating the fungi, or the plants, seeds, materials or soil to be protected against fungal infection, with a fungicidally active amount of the active ingredients. They are used before or after infection of the materials, plants or seeds by the fungi.

They can be converted into the customary formulations, such as solutions, emulsions, suspensions, dusts, powders, pastes and granules. The use form depends in each case on the intended purpose; in any case, it should guarantee fine and uniform distribution of the compounds according to the invention. The formulations are prepared in a known manner, eg. by extending the active ingredient with solvents and/or carriers, if desired using emulsifiers and dispersants, it also being possible for other organic solvents to be used as auxiliary solvents if water is used as the diluent. Suitable auxiliaries are essentially: solvents such as aromatics, (eg. xylene), chlorinated aromatics (eg. chlorobenzenes), paraffins (eg. mineral oil fractions), alcohols (eg. methanol, butanol), ketones (eg. cyclohexanone), amines (eg.ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkyl-sulfonates and arylsulfonates), and dispersants such as lignine-sulfite waste liquors and methylcellulose.

In general, the fungicidal compositions comprise from 0.1 to 95, preferably from 0.5 to 90%, by weight of active ingredient.

When used in crop protection, the rates of application are from 0.01 to 2.0 kg of active ingredient per ha, depending on the nature of the desired effect.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the field of application and the desired effect. Usual rates of application in the protection of materials are, for example, from 0.001 g to 2 kg, preferably 0.005 g to 1 kg, of active ingredient per cubic meter of material treated.

In the use form as fungicides, the agents according to the invention may also be present together with other active ingredients, eg. with herbicides, insecticides, growth regulators, fungicides or else fertilizers.

A mixture of fungicides frequently results in a widened fungicidal spectrum of action.

The following list of fungicides together with which the compounds according to the invention can be used is intended to illustrate the possible combinations, but not to impose any limitation: sulfur, dithiocarbamate and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc-(N,N'-propylenebisdithiocarbamate), N,N'-polypropylenebis (thiocarbamoyl)disulfide;

nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenyl isopropylcarbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2, 4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatothiobenzothiazole, 1,4-dichloro-2, 5-dimethoxybenzene, 4-(2-chlorophenylhydrazono)-3-methyl-5-isoxazolone, pyridine-2-thiol-1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine-4,4-dioxid, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxycyclohexylamide, N-cyclohexyl-N-methoxy-2, 5-dimethylfuran-3-carboxamide, 2-methylbenzanilide, 2-iodobenzanilide, N-formyl-N-morpholine 2,2,2-trichloroethyl acetal, piperazine-1,4-diylbis(2,2,2-trichloroethyl)formamide, 1-(3,4-dichloroanilino)-1-formylamino-2,2,2-trichloroethane, 2,6-dimethyl-N-tridecyl-morpholine and its salts, 2,6-dimethyl-N-cyclododecylmorpholine and its salts, N-[3-(p-tert-butylphenyl)-2-methylpropyl]-cis-2,6-dimethyl-morpholine, N-[3-(p-tert-butylphenyl)- 2-methylpropyl] piperidine, 1- [2-(2, 4-dichlorophenyl)-4- ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-but anone, 1-(4-chlorophenoxy)-3,3-dimethyl-l-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis (p-chlorophenyl) -3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D, L-2-aminobutyrolactone, DL-N- (2,6-dimethylphenyl)-N-(phenylacetyl)alanine methyl ester, 5-methyl-5-vinyl-3- (3,5-dichlorophenyl)-2,4-dioxo-1, 3-oxazolidine, 3-[3,5-dichlorophenyl-5-methyl-5-methoxymethyl]-1,3-oxazolidine-2,4-dione, 3-(3,5-dichlorophenyl)-1-isopropylcarbamoylhydantoin, N-(3,5-dichlorophenyl) -1,2-dimethylcyclopropane-1, 2-dicarboximide, 2-cyano-[N-(ethylaminocarbonyl)-2-methoximino] acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2, 6-dinitro-4-trifluoromethylphenyl) -5-trifluoromethyl-3-chloro-2-aminopyridine, 1-((bis (4-fluorophenyl)-methylsilyl)methyl)1H-1,2,4-triazole;

strobilurins such as methyl E-methoxyimino-[α-(o-tolyloxy)-o-tolyl]acetate, methyl E-2-[2-[6-(2-cyanophenoxy)-pyrimidin-4-yloxy]phenyl]-3-methoxyacrylate, methyl E-methoxyimino-[α-(2-phenoxyphenyl)]acetamide, methyl E-methoxyimino-[α-(2, 5-dimethylphenoxy) -o-tolyl]acetamide;

anilinopyrimidines such as N-(4,6-dimethylpyrimidin-2-yl) aniline, N-[4-methyl-6-(1-propynyl)pyrimidin-2-yl] aniline, N-(4-methyl-6-cyclopropylpyrimidin-2-yl) aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxyphenyl) acryloylmorpholine.

The compounds of the formula I are furthermore suitable for effectively controlling animal pests from the classes of the insects, arachnids and nematodes. They can be employed as pesticides in crop protection and in the hygiene, stored-product and veterinary sector.

The harmful insects include from the order of the lepidopterans (Lepidoptera), for example, *Agrotis ypsilon, Agro-* tis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucopta coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, ChrysoMya bezziana, ChrysoMya hominivorax, ChrysoMya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, HyleMyia platura, Hypoderma lineata, LirioMyza sativae, LirioMyza trifolii, Lucilia caprina, Lucilia cuprina, Lucilia sericata, Lycoria pectoralis, Mayetiola destructor, Musca domestica, Muscina stabulans, Oestrus ovis, Oscinella frit, PegoMya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the hepteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris: Lygus pratensis, Nezara viridula, Piesma quadrata, Solubea insularis, Thyanta perditor.*

From the order of homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina), such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root-knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they should guarantee the finest possible distribution of the active ingredients according to the invention.

The active ingredient concentrations in the ready-to-use preparations can be varied within substantial ranges.

In general, they are between 0.0001 and 10%, preferably between 0.01 and 1%.

The active ingredients can also be used successfully in the ultra-low-volume method (ULV), it being possible to apply formulations comprising over 95% by weight of active ingredient, or even the active ingredient without additives.

The rate of application of active ingredient for controlling pests is from 0.1 to 2.0, preferably 0.2 to 1.0 kg/ha under field conditions.

Substances which are suitable for preparing directly sprayable solutions, emulsions, pastes or oil dispersions are mineral oil fractions of medium to high boiling point, such as kerosene or diesel oil, furthermore cold tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agents, tackifier, dispersant or emulsifier. Alternatively, it is possible to prepare concentrates composed of active ingredient, wetting agent, tackifier, dispersant or emulsifier and, if desired, solvent or oil, and these concentrates are suitable for dilution with water.

Suitable surfactants are alkali metal, alkaline earth metal and ammonium salts of lignin sulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene, or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensate, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, materials for spreading or dusts can be prepared by mixing or jointly grinding the active ingredients with a solid carrier.

In general, the formulations comprise between 0.01 and 95% by weight, preferably between 0.1 and 90% by weight, of the active ingredient. The active ingredients are employed in a purity of from 90 to 100%, preferably 95% to 100% (according to NMR-spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of the silica gel. This gives a formulation of the active ingredient with good adhesion (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide to 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide to 1 mol of isooctylphenol and 5 parts by weight of the adduct of 40 mol of ethylene oxide to 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

VIII. 20 parts by weight of a compound according to the invention are mixed thoroughly with 3 parts by weight sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20000 parts by weight of water give the spray mixture which comprises 0.1% by weight of active ingredient.

Granules, eg. coated granules, impregnated granules and homogeneous granules, can be prepared by binding the active ingredients to solid carriers. Examples of solid carriers are mineral earths, such as silicas, silica gels, silcates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas and products of vegetable origin, such as cereal meal, tree bark meal, wood meal and nutshell meal, cellulose powders and other solid carriers.

Various types of oils, or herbicides, fungicides, other pesticides or bactericides can be admixed with the active ingredients, if desired also only just before use (tank mix). These agents can be admixed with the agents according to the invention in a weight ratio of from 1:10 to 10:1.

SYNTHESIS EXAMPLES

The protocols given in the synthesis examples below were used for obtaining other compounds I by altering the starting materials as required. The resulting compounds are given in the table below together with physical data.

Example 1

Methyl E-2-methoxyimino-2-[(2-[2-(benzyloximinoeth-1'-yl)-pyrimidin-4-yl)] oxymethyl)phenyl]acetate (Compound No. I.38)

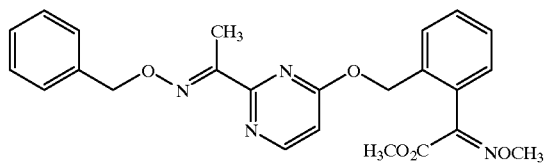

Stage 1: 4-Hydroxy-2-(benzyloximinoeth-1'-yl)pyrimidine

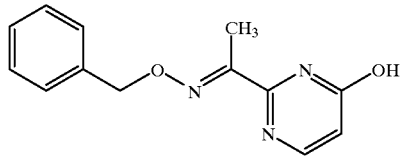

2.6 g of 4-hydroxy-2-acetylpyrimidine hydrochloride, 3 g of 20% strength aqueous sodium hydroxide solution and 2.16 g of benzyloxyamine hydrochloride were introduced into 35 ml of methanol, and the mixture was brought to pH 5 using 10% strength aqueous HCl. It was then stirred for four hours at 40° C. and then for 14 hours at room temperature. The reaction mixture was concentrated. The crude product which remained was taken up in methyl tert-butyl ether. The combined organic phases were washed with water and dried. The mixture was reconcentrated. The crude product which remained was purified on silica gel using ethyl acetate. This gave 2.6 g of 4-hydroxy-2-(benzyloximinoeth-1'-yl) pyrimidine as a pale yellow solid (m.p.: 142–143° C.).

Stage 2: Title compound 1.82 g of 4-Hydroxy-2-(benzyloximinoeth-1'-yl) pyrimidine, 2.15 g of methyl E-2-methoxyimino-2-[2-(bromomethyl)phenyl]acetate and 1.55 g of potassium carbonate were stirred in 30 ml of dimethylformamide for 4 hours at 50° C. and then for 14 hours at room temperature. The reaction mixture was treated with water and subsequently extracted using methyl tert-butyl ether. The combined organic phases were washed with water, dried over sodium sulfate and reconcentrated. The crude product which remained was purified on silica get using cyclohexane/methyl tert-butyl ether 1:1. This gave 1.7 g of the title compound as a pale resin.

IR (cm$^{-1}$): 1728, 1567, 1440, 1323, 1288, 1220, 1069, 1046, 1019, 986.

Example 2

N-Methyl-E-2-methoxyimino-2-[(2-[(2-(benzyloximinoeth-1'-yl)-pyrimidin-4-yl)] oxymethyl)phenyl]-acetamide (Compound No. I.39)

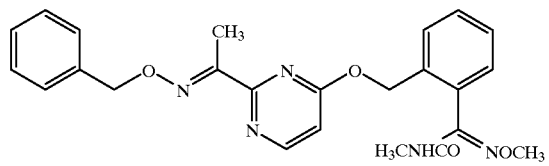

4.4 g of the methyl ester (title compound of Example 1) were dissolved in 80 ml of tetrahydrofuran and treated with 3.0 g of 40% strength aqueous methyl amine solution. The mixture was stirred for 5 hours at 45° C. When cold, the reaction mixture was concentrated. The residue which remained was taken up in 100 ml of methyl tert-butyl ether. The organic phase was washed with water, dried over sodium sulfate and subsequently evaporated to dryness. 4.3 g of the title compound remained as a colorless solid (m.p.: 83–84° C.).

Example 3

Methyl E-2-methoxyimino-2-[(2-[2-ethyl-6-(methoximinoeth-1'-yl)-pyrimidin-4-yl)]oxymethyl) phenyl]acetate (Compound No. I.1)

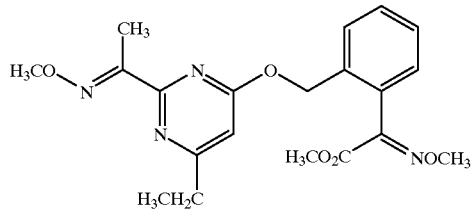

Stage 1: Ethyl 3-(2-methyl-1,3-dioxolan-2-yl)-3-oxopropionate

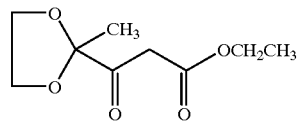

236 g of potassium tert-butylate were suspended in 1.3 l of diethyl carbonate and the suspension was heated at 60° C. At this temperature, 1 mol of 2-methyl-2-acetyl-1,3-dioxolane, dissolved in 500 ml of diethyl carbonate, was added dropwise in the course of three hours. Stirring was continued for three hours at 60° C. When cold, the mixture was poured into 2 l of 10%- strength sulfuric acid, the organic phase was separated off and the aqueous phase was extracted using ethyl acetate. Drying of the combined organic phases and evaporation of the diethyl carbonate gave, as the residue, the crude product which was purified by distillation in vacuo. This gave the product in a yield of 65 % (b.p.: 69–72° C./0.08 mbar).

Stage 2: 4-Hydroxy-2-ethyl-6-(2-methyl-1,3-dioxolan-2-yl)pyrimidine

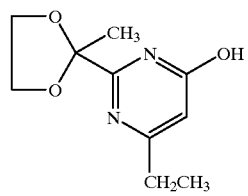

54.3 g of propionamidine hydrochloride were dissolved in 350 ml ethanol. 90 g of 30% strength sodium methanolate solution were added dropwise in the course of 30 minutes and the mixture was stirred for 15 minutes. 101 g of the product of stage 1 were then added dropwise in the course of one hour. The mixture was refluxed for eight hours and stirring was then continued for 14 hours. The reaction mixture was concentrated. The residue which remained was dissolved in 320 ml of 10% strength sodium hydroxide solution and then washed three times using in each case 150 ml of methyl tert-butyl ether. The aqueous phase was brought to pH 5 with hydrochloric acid. The product, which as a result, precipitated was filtered off and dried. This gave 47,6 g of the product as a colorless solid (m.p.: 117–120° C.).

Stage 3: 4-Hydroxy-2-ethyl-6-acetylpyrimidine

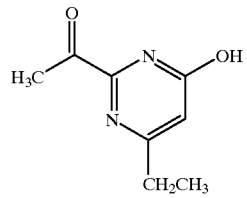

20 g of the pyrimidine of Stage 2 were introduced into 200 ml dioxane. 100 ml of 5N hydrochloric acid were added dropwise at room temperature. The mixture was refluxed for three hours. When cold, the reaction mixture was poured onto ice, neutralized using dilute sodium hydroxide solution, saturated with sodium chloride and extracted using ethyl acetate. The combined organic phases were dried. Evaporation of the solvent gave, as the residue, the product as a colorless solid (m.p.: 153–155° C.).

Stage 4: Methyl E-2-methoxyimino-2-[(2-[2-ethyl-6-acetyl-pyrimidin-4-yl)]oxymethyl)phenyl]acetate

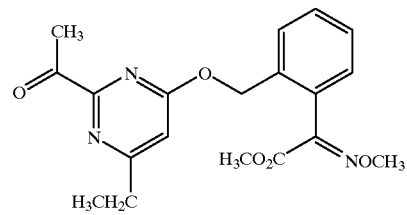

7 g of the pyrimidine from Stage 3, 12 g of methyl E-2-methoxyimino-2-[2-(bromomethyl)phenyl]acetate and 10 g of potassium carbonate were stirred for 8 hours at 60° C. in 250 ml of dimethylformamide. The reaction mixture was filtered. The residue which remained after concentration of the filtrate was dissolved in ethyl acetate. This organic phase was washed with dilute sodium hydroxide solution and then with water, dried over sodium sulfate and reconcentrated. The crude product which remained was employed in Stage 5 without further purification.

Stage 5: Title compound 2 g of the product of Stage 4 and 0.5 g of methoxyamine hydrochloride were refluxed for 6 hours in 100 ml of methanol. When cold, the mixture was filtered. The residue which remained after the filtrate had been concentrated was dissolved in ethyl acetate. This organic phase was washed with water, dried over sodium sulfate and reconcentrated. The crude product which remained was purified on silica gel using heptane/ethyl acetate 8:2. This gave 1 g of the title compound as a colorless solid.(m.p.: 90–92° C.).

Example 4

N-Methyl-E-2-methoxyimino-2-[(2-[2-ethyl-6-(methoximinoeth-1'-yl)pyrimidin-4-yl)]oxymethyl)phenyl]acetamide (Compound No. I.23)

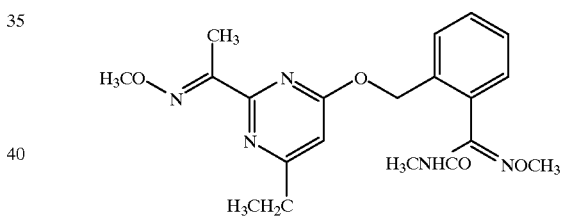

0.3 g of the methyl ester (title compound of Example 3) was dissolved in 100 ml of tetrahydrofuran and treated with 50 ml of 40% strength aqueous methyl amine solution. The mixture was stirred for 8 hours at 40° C. When cold, the batch was concentrated. The residue which remained was taken up in 100 ml of methyl tert-butyl ether. The organic phase was washed with water, dried over sodium sulfate and subsequently evaporated to dryness. 0.3 g of the title compound remained as a pale resin.

TABLE I

| No. | R¹ | R² | R³ | n | # | R⁴ | R⁵_y | Q | Physical Data[a] |
|---|---|---|---|---|---|---|---|---|---|
| I.1 | $CH_3$ | $CH_3$ | H | 1 | 6 | 2-$CH_2CH_3$ | H | $C(CO_2CH_3)=NOCH_3$ | 90–92 |
| I.2 | $CH_2CH_3$ | $CH_3$ | H | 1 | 6 | 2-$CH_2CH_3$ | H | $C(CO_2CH_3)=NOCH_3$ | resin |
| I.3 | $(CH_2)_2CH_3$ | $CH_3$ | H | 1 | 6 | 2-$CH_2CH_3$ | H | $C(CO_2CH_3)=NOCH_3$ | resin |
| I.4 | $CH_3$ | $CH_3$ | H | 1 | 6 | 2-$CH_2CH_3$ | H | $C(CO_2CH_3)=CHOCH_3$ | resin |
| I.5 | $CH_2CH_3$ | $CH_3$ | H | 1 | 6 | 2-$CH_2CH_3$ | H | $C(CO_2CH_3)=CHOCH_3$ | resin |
| I.6 | $(CH_2)_2CH_3$ | $CH_3$ | H | 1 | 6 | 2-$CH_2CH_3$ | H | $C(CO_2CH_3)=CHOCH_3$ | resin |
| I.7 | $CH_2CH=CH_2$ | $CH_3$ | H | 1 | 6 | 2-$CH_2CH_3$ | H | $C(CO_2CH_3)=CHOCH_3$ | resin |
| I.8 | $(CH_2)_3CH_3$ | $CH_3$ | H | 1 | 6 | 2-$CH_2CH_3$ | H | $C(CO_2CH_3)=CHOCH_3$ | resin |
| I.9 | $CH_2CH_3$ | $CH_3$ | H | 1 | 6 | 2-$CH_3$ | H | $C(CO_2CH_3)=NOCH_3$ | 103–106 |
| I.10 | $(CH_2)_2CH_3$ | $CH_3$ | H | 1 | 6 | 2-$CH_3$ | H | $C(CO_2CH_3)=NOCH_3$ | resin |
| I.11 | $CH_3$ | $CH_3$ | H | 1 | 6 | 2-$(CH_2)_2CH_3$ | H | $C(CO_2CH_3)=NOCH_3$ | resin |
| I.12 | $CH_2CH_3$ | $CH_3$ | H | 1 | 6 | 2-$(CH_2)_2CH_3$ | H | $C(CO_2CH_3)=NOCH_3$ | resin |
| I.13 | $(CH_2)_2CH_3$ | $CH_3$ | H | 1 | 6 | 2-$(CH_2)_2CH_3$ | H | $C(CO_2CH_3)=NOCH_3$ | resin |
| I.14 | $CH_2CH=CH_2$ | $CH_3$ | H | 1 | 6 | 2-$(CH_2)_2CH_3$ | H | $C(CO_2CH_3)=NOCH_3$ | resin |
| I.15 | $CH_3$ | $CH_3$ | H | 1 | 6 | 2-$CH_3$ | H | $C(CO_2CH_3)=CHOCH_3$ | resin |
| I.16 | $CH_2CH_3$ | $CH_3$ | H | 1 | 6 | 2-$CH_3$ | H | $C(CO_2CH_3)=CHOCH_3$ | resin |
| I.17 | $CH_3$ | $CH_3$ | H | 1 | 6 | 2-$(CH_2)_2CH_3$ | H | $C(CO_2CH_3)=CHOCH_3$ | resin |
| I.18 | $CH_2CH_3$ | $CH_3$ | H | 1 | 6 | 2-$(CH_2)_2CH_3$ | H | $C(CO_2CH_3)=CHOCH_3$ | resin |
| I.19 | $(CH_2)_2CH_3$ | $CH_3$ | H | 1 | 6 | 2-$(CH_2)_2CH_3$ | H | $C(CO_2CH_3)=CHOCH_3$ | resin |
| I.20 | $CH_2CH=CH_2$ | $CH_3$ | H | 1 | 6 | 2-$(CH_2)_2CH_3$ | H | $C(CO_2CH_3)=CHOCH_3$ | resin |
| I.21 | $(CH_2)_3CH_3$ | $CH_3$ | H | 1 | 6 | 2-$(CH_2)_2CH_3$ | H | $C(CO_2CH_3)=CHOCH_3$ | resin |
| I.22 | $CH_3$ | $CH_3$ | H | 1 | 6 | 2-$CH_3$ | H | $C(CO_2CH_3)=NOCH_3$ | resin |
| I.23 | $CH_3$ | $CH_3$ | H | 1 | 6 | 2-$CH_2CH_3$ | H | $C(CONHCH_3)=NOCH_3$ | resin |
| I.24 | $CH_2CH_3$ | $CH_3$ | H | 1 | 6 | 2-$CH_3$ | H | $C(CONHCH_3)=NOCH_3$ | resin |
| I.25 | $CH_3$ | $CH_3$ | H | 1 | 2 | H | H | $C(CONHCH_3)=NOCH_3$ | 1670, 1568, 1527, 1461, 1441, 1324, 1290, 1048, 979 |
| I.26 | $CH_2CH_3$ | $CH_3$ | H | 1 | 2 | H | H | $C(CO_2CH_3)=NOCH_3$ | 67–68 |
| I.27 | $CH_2CH_3$ | $CH_3$ | H | 1 | 2 | H | H | $C(CONHCH_3)=NOCH_3$ | 1671, 1568, 1527, 1441, 1323, 1292, 1091, 1047, 1000, 980 |
| I.28 | $(CH_2)_2CH_3$ | $CH_3$ | H | 1 | 2 | H | H | $C(CO2CH_3)=NOCH_3$ | 1728, 1567, 1440, 1323, 1288, 1220, 1069, 1047, 1020, 985 |
| I.29 | $(CH_2)_2CH_3$ | $CH_3$ | H | 1 | 2 | H | H | $C(CONHCH_3)=NOCH_3$ | 1672, 1568, 1526, 1441, 1324, 1291, 1038, 1004, 980 |
| I.30 | $CH(CH_3)_2$ | $CH_3$ | H | 1 | 2 | H | H | $C(CO_2CH_3)=NOCH_3$ | 78–80 |
| I.31 | $CH(CH_3)_2$ | $CH_3$ | H | 1 | 2 | H | H | $C(CONHCH_3)=NOCH_3$ | 100–102 |
| I.32 | $(CH_2)_3CH_3$ | $CH_3$ | H | 1 | 2 | H | H | $C(CO_2CH_3)=NOCH_3$ | 1729, 1567, 1440, 1323, 1287, 1220, 1069, 1045, 1020, 985 |
| I.33 | $(CH_2)_3CH_3$ | $CH_3$ | H | 1 | 2 | H | H | $C(CONHCH_3)=NOCH_3$ | 1671, 1568, 1527, 1440, 1324, 1291, 1037, 979 |
| I.34 | $CH_2CH(CH_3)_2$ | $CH_3$ | H | 1 | 2 | H | H | $C(CO_2CH_3)=NOCH_3$ | 1729, 1567, 1462, 1440, 1323, 1288, 1220, 1079, 1039, 1021 |
| I.35 | $CH_2CH(CH_3)_2$ | $CH_3$ | H | 1 | 2 | H | H | $C(CONHCH_3)=NOCH_3$ | 1671, 1568, 1527, 1462, 1440, 1324, 1292, 1038, 979 |
| I.36 | $CH(CH_3)CH_2CH_3$ | $CH_3$ | H | 1 | 2 | H | H | $C(CO_2CH_3)=NOCH_3$ | 1729, 1566, 1461, 1440, 1322, 1287, 1220, 1070, 1017, 986 |
| I.37 | $CH(CH_3)CH_2CH_3$ | $CH_3$ | H | 1 | 2 | H | H | $C(CONHCH_3)=NOCH_3$ | 98–100 |
| I.38 | $CH_2-C_6H_5$ | $CH_3$ | H | 1 | 2 | H | H | $C(CO_2CH_3)=NOCH_3$ | 1728, 1567, 1440, 1323, 1288, 1220, 1069, 1046, 1019, 986 |
| I.39 | $CH_2-C_6H_5$ | $CH_3$ | H | 1 | 2 | H | H | $C(CONHCH_3)=NOCH_3$ | 83–84 |

[a]: m.p. (° C.); IR (cm$^{-1}$); ¹H NMR (δ in ppm)

Examples of the activity against harmful fungi

The fungicidal activity of the compounds of the general formula I was demonstrated by the following experiments:

The active ingredients were formulated as a 20% strength emulsion in a mixture of 70% by weight of cyclohexanone, 20% by weight of Nekanil® LN (Lutensol® AP6, wetting agent having emulsifying and dispersant action based on the ethoxylated alkylphenols) and 10% by weight of Emulphor® EL (Emulan® EL, emulsifier based on ethoxylated fatty alcohols) and diluted with water to give the desired concentration.

Activity against Plasmopara viticola (downy mildew of grapevine)

Grapevines in pots (cultivar: "Muller Thurgau") were sprayed to drip point with the preparation of the active ingredient (rate of application: 250 ppm). After 8 days, the plants were sprayed with zoo spore suspension of the fungus *Plasmopara viticola* and left to stand for 5 days at 20–30° C. and high atmospheric humidity. Prior to assessment, the plants were then left to stand at high atmospheric humidity for 16 hours. Evaluation was carried out visually.

In this test, the disease level of the plants which had been treated with the compounds 1, 3, 5, 7, 11, 14, 17, 18, 20, 22, 25, 26, 27, 28, 29, 30, 31, 32, 33, 34, 35, 36, 37, 38 and 39 according to the invention was 15%, while the untreated (control) plants showed a disease level of 80%.

Examples of the activity against animal pests

The activity of the compounds of the general formula I against animal pests was demonstrated by the following experiments:

The active ingredients were formulated a. as a 0.1% strength solution in acetone or b. as a 10% strength emulsion in a mixture of 70% by weight of cyclohexanone, 20% by weight of Nekanil® LN (Lutensol® AP6, wetting agent having emulsifying and dispersant action based on the ethoxylated alkylphenols) and 10% by weight of Emulphor® EL (Emulan® EL, emulsifier based on ethoxylated fatty alcohols) and diluted to give the desired concentration, using acetone in the case of a. and water in the case of b.

After conclusion of the experiments, the lowest concentration was determined in each case at which the compounds still caused an 80 to 100% inhibition or mortality in comparison to untreated controls (limit or minimal concentration).

What is claimed is:

1. A pyrimidyl phenyl or pyrimidyl benzyl ether of the formula I

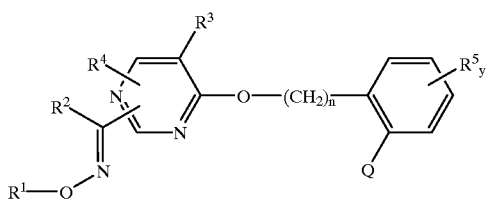

or a salt or N-oxide thereof, where the substituents and indices have the following meanings:

Q is $C(CO_2CH_3)=CHCH_3$, $C(CO_2CH_3)=CHOCH_3$, $C(CO_2CH_3)=NOCH_3$, $C(CONHCH_3)=NOCH_3$ or $N(OCH_3)-CO_2CH_3$;

n is 0 or 1;

$R^1$ is $C_1-C_6$-alkyl or aryl-$C_1-C_2$-alkyl, it being possible for the aryl radical to be partially or fully halogenated and/or to carry one to three of the following groups: $C_1-C_4$-alkyl, $C_1-C_4$-haloalkyl, $C_1-C_4$-alkoxy;

$R^2$ is hydrogen, $C_1-C_6$-alkyl, $C_2-C_6$-alkenyl, $C_2-C_6$-alkynyl. $C_3-C_6$-cycloalkyl or aryl:

$R^3$ is hydrogen, halogen, $C_1-C_4$-alkyl or $C_1-C_2$-haloalkyl;

$R^4$ is hydrogen, halogen, $C_1-C_2$-alkyl, $C_1-C_2$-alkoxy, cyano or nitro:

y is 0, 1, 2 or 3, it being possible for the radicals $R^5$ to be different if y is 2 or 3;

$R^5$ is cyano, halogen, $C_1-C_4$-alkyl, $C_1-C_4$-haloalkyl or $C_1-C_4$-alkoxy.

2. A process for the preparation of a compound I as defined in claim 1, which comprises converting a pyrimidine derivative of the formula IIa

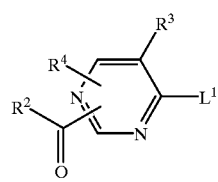

where $L^1$ is a nucleophilically exchangeable leaving group with a phenol or a benzyl alcohol of the formula IIIa

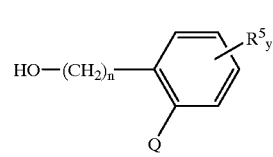

in an inert solvent to give the corresponding ether of the formula IVa

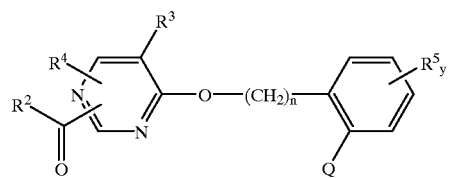

and subsequently reacting IVa with an O-substituted hydroxylamine ($R^1$—O—$NH_2$) or a salt thereof to give I.

3. A composition which is suitable for controlling pests or harmful fungi, comprising a solid or liquid carrier and a compound of the formula I as claimed in claim 1.

4. A method for controlling harmful fungi, which comprises treating the fungi, or the materials, plants, the soil or seed to be protected against fungal attack, with an effective amount of a compound of the formula I as desired in claim 1.

5. A method for controlling pests, which comprises treating the pests, or the materials, plants, the soil or seed to be protected against them, with an effective amount of a compound of the defined formula I as claimed in claim 1.

6. A pyrimidyl phenyl or pyrimidal benzyl ether as claimed in claim 1 wherein Q in formula I is $C(COOCH_3)=CHOCH_3$.

7. A pyrimidyl phenyl or pyrimidal benzyl ether as claimed in claim 1 wherein Q in formula I is $C(COOCH_3)=NOCH_3$ or $C(CONHCH_3)=NOCH_3$.

* * * * *